United States Patent
Boden, Jr. et al.

(10) Patent No.: US 10,850,081 B2
(45) Date of Patent: Dec. 1, 2020

(54) IMPLANTABLE BODILY FLUID DRAINAGE VALVE WITH MAGNETIC FIELD RESISTANCE ENGAGEMENT CONFIRMATION

(71) Applicant: Integra LifeSciences Switzerland Sarl, Le Locle (CH)

(72) Inventors: Thomas Boden, Jr., Middleboror, MA (US); Patricia D'Aoust, Franklin, MA (US); Alexander Arazawa, Cambridge, MA (US)

(73) Assignee: Integra LifeSciences Switzerland Sáarl, Le Locle (CH)

( * ) Notice: Subject to any disclaimer, the term of this patent is extended or adjusted under 35 U.S.C. 154(b) by 499 days.

(21) Appl. No.: 15/708,549

(22) Filed: Sep. 19, 2017

(65) Prior Publication Data
US 2019/0083764 A1    Mar. 21, 2019

(51) Int. Cl.
*A61M 27/00*    (2006.01)

(52) U.S. Cl.
CPC ....... *A61M 27/006* (2013.01); *A61M 2205/18* (2013.01); *A61M 2205/3317* (2013.01); *A61M 2205/52* (2013.01); *A61M 2205/582* (2013.01); *A61M 2205/583* (2013.01)

(58) Field of Classification Search
CPC .......... A61M 27/006; A61M 2205/103; A61M 2205/3317; A61M 2205/3331; A61M 2205/3515; A61M 2205/50; A61M 2205/583; A61M 2205/6054; A61M 2205/70; G01R 33/005; G01R 33/0076
See application file for complete search history.

(56) References Cited

U.S. PATENT DOCUMENTS

| | | | |
|---|---|---|---|
| 3,902,252 | A | 9/1975 | Farber |
| 4,173,228 | A | 11/1979 | Van Steenwyk et al. |
| 4,595,390 | A | 6/1986 | Hakim et al. |
| 4,608,992 | A | 9/1986 | Hakim et al. |
| 4,622,644 | A | 11/1986 | Hansen |

(Continued)

FOREIGN PATENT DOCUMENTS

EP    2 826 517    1/2015

OTHER PUBLICATIONS

Copending, co-owned U.S. Appl. No. 15/708,404, filed Sep. 19, 2017.

(Continued)

*Primary Examiner* — Benjamin J Klein
(74) *Attorney, Agent, or Firm* — Cohen & Hildebrand, PLLC

(57) ABSTRACT

Verifying whether a magnetic field resistance mechanism is properly engaged in a drainage valve having an adjustable valve unit including a rotating construct and a pair of primary magnetic elements for programming the valve unit. Using a toolset, a determination is made whether the magnetic field resistance mechanism is properly engaged. An alert is generated whether the magnetic field resistance mechanism is at least one of properly engaged or not properly engaged based on: (i) a measured angular position of a detected one of the pair of primary magnetic elements relative to a direction of flow of fluid through the valve; and/or (ii) a measured distance separation between respective centers of the pair of primary magnetic elements.

14 Claims, 24 Drawing Sheets

(56) References Cited

U.S. PATENT DOCUMENTS

| | | |
|---|---|---|
| 4,839,809 A | 6/1989 | Leighton et al. |
| 5,309,096 A | 5/1994 | Hoegnelid |
| 5,425,382 A | 6/1995 | Golden et al. |
| 5,438,990 A | 8/1995 | Wahlstrand et al. |
| 5,525,901 A | 6/1996 | Clymer et al. |
| 5,643,194 A | 7/1997 | Negre |
| 5,709,225 A | 1/1998 | Budgifvars et al. |
| 5,758,667 A | 6/1998 | Slettenmark |
| 5,879,297 A | 3/1999 | Haynor et al. |
| 6,101,417 A | 8/2000 | Vogel et al. |
| 6,129,668 A | 10/2000 | Haynor et al. |
| 6,138,681 A | 10/2000 | Chen et al. |
| 6,216,028 B1 | 4/2001 | Haynor et al. |
| 6,242,907 B1 | 6/2001 | Clymer et al. |
| 6,263,230 B1 | 7/2001 | Haynor et al. |
| 6,439,538 B1 | 8/2002 | Ito |
| 6,485,449 B2 | 11/2002 | Ito |
| 6,690,159 B2 | 2/2004 | Burreson et al. |
| 6,702,249 B2 | 3/2004 | Ito |
| 6,707,293 B2 | 3/2004 | Wan et al. |
| 6,850,803 B1 | 2/2005 | Jimenez et al. |
| 6,882,146 B2 | 4/2005 | Maiwald |
| 6,883,241 B2 | 4/2005 | Moskowitz et al. |
| 6,891,367 B2 | 5/2005 | Shinmura et al. |
| 6,937,906 B2 | 8/2005 | Terry et al. |
| 6,951,059 B2 | 10/2005 | Moskowitz et al. |
| 7,126,331 B2 | 10/2006 | Johnson et al. |
| 7,173,419 B1 | 2/2007 | Johnson et al. |
| 7,228,252 B2 | 6/2007 | Alexander et al. |
| 7,301,332 B2 | 11/2007 | Govari et al. |
| 7,334,582 B2 | 2/2008 | Bertrand et al. |
| 7,525,309 B2 | 4/2009 | Sherman et al. |
| 7,753,913 B2 | 7/2010 | Szakelyhidi, Jr. et al. |
| 7,842,004 B2 | 11/2010 | Kassem |
| 7,856,987 B2 | 12/2010 | Bertrand et al. |
| 7,921,571 B2 | 4/2011 | Moureaux et al. |
| 7,945,334 B2 | 5/2011 | Jimenez et al. |
| 8,015,977 B2 | 9/2011 | Bertrand et al. |
| 8,038,641 B2 | 10/2011 | Soares et al. |
| 8,148,978 B2 | 4/2012 | Sherman et al. |
| 8,241,240 B2 | 8/2012 | Murphy |
| 8,257,296 B2 | 9/2012 | Bertrand et al. |
| 8,322,365 B2 | 12/2012 | Wilson et al. |
| 8,398,617 B2 | 3/2013 | Ginggen et al. |
| 8,518,023 B2 | 8/2013 | Roth et al. |
| 8,539,956 B2 | 9/2013 | Bertrand et al. |
| 8,591,499 B2 | 11/2013 | Girardin et al. |
| 8,617,142 B2 | 12/2013 | Wilson et al. |
| 8,622,978 B2 | 1/2014 | Bertrand et al. |
| 8,630,695 B2 * | 1/2014 | Negre ............. A61B 5/06 128/899 |
| 8,733,394 B2 | 5/2014 | Negre et al. |
| 8,753,331 B2 | 6/2014 | Murphy |
| 8,862,200 B2 | 10/2014 | Sherman et al. |
| 9,126,010 B2 | 9/2015 | Shah et al. |
| 9,149,615 B2 | 10/2015 | Wilson |
| 9,220,876 B2 | 12/2015 | Girardin et al. |
| 9,242,077 B2 | 1/2016 | Wilson et al. |
| 9,295,826 B2 | 3/2016 | Bertrand et al. |
| 9,364,646 B2 | 6/2016 | Bertrand et al. |
| 9,381,301 B2 | 7/2016 | Lattanzio et al. |
| 9,427,559 B2 | 8/2016 | Shah et al. |
| 9,453,934 B2 | 9/2016 | Hughes |
| 9,585,600 B2 | 3/2017 | Sharonov |
| 2004/0017192 A1 | 1/2004 | Clymer et al. |
| 2004/0055610 A1 | 3/2004 | Forsell |
| 2004/0064030 A1 | 4/2004 | Forsell |
| 2004/0097803 A1 | 5/2004 | Panescu |
| 2004/0250820 A1 | 12/2004 | Forsell |
| 2005/0092335 A1 * | 5/2005 | Bertrand ............. A61B 5/06 128/899 |
| 2005/0187509 A1 | 8/2005 | Wolf |
| 2006/0124140 A1 | 6/2006 | Forsell |
| 2007/0276218 A1 | 11/2007 | Yellen |
| 2010/0010338 A1 | 1/2010 | van Dam et al. |
| 2010/0292759 A1 | 11/2010 | Hahn et al. |
| 2011/0031961 A1 | 2/2011 | Durand et al. |
| 2012/0041297 A1 | 2/2012 | McGary |
| 2012/0302938 A1 | 11/2012 | Browd et al. |
| 2013/0197422 A1 | 8/2013 | Browd et al. |
| 2014/0336560 A1 | 11/2014 | Hakim |
| 2015/0196742 A1 | 7/2015 | Browd et al. |
| 2016/0089519 A1 | 3/2016 | Bittenson |
| 2016/0166813 A1 | 6/2016 | Bertrand et al. |
| 2016/0184563 A1 | 6/2016 | Bertrand et al. |
| 2016/0279396 A1 | 9/2016 | Bertrand et al. |
| 2017/0095650 A1 | 4/2017 | Wilson |
| 2017/0209056 A1 | 7/2017 | Browd et al. |
| 2018/0001064 A1 * | 1/2018 | Pfleiderer ............. A61M 27/006 |
| 2018/0015266 A1 * | 1/2018 | Amery ............. G01D 7/00 |
| 2018/0126147 A1 | 5/2018 | Hakim |
| 2018/0184943 A1 * | 7/2018 | Boden, Jr. ............. A61B 5/062 |
| 2018/0243542 A1 | 8/2018 | Pfleiderer et al. |

OTHER PUBLICATIONS

Copending, co-owned U.S. Appl. No. 15/708,496, filed Sep. 19, 2017.

Copending, co-owned U.S. Appl. No. 15/708,600, filed Sep. 19, 2017.

* cited by examiner

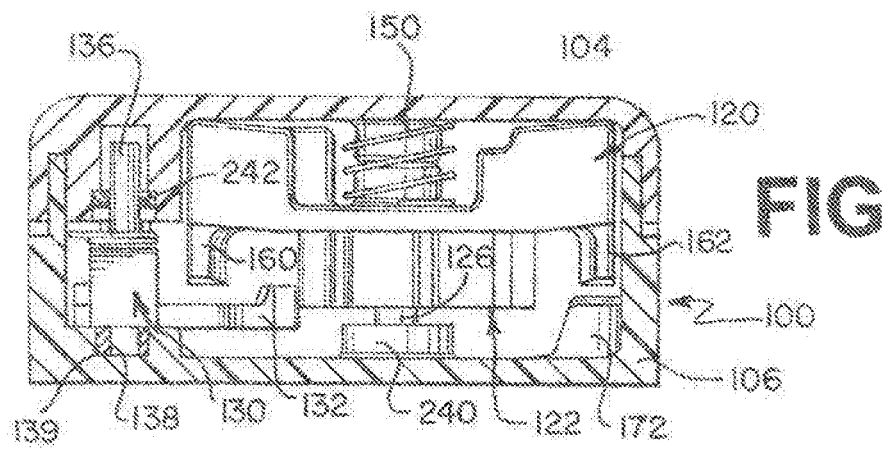
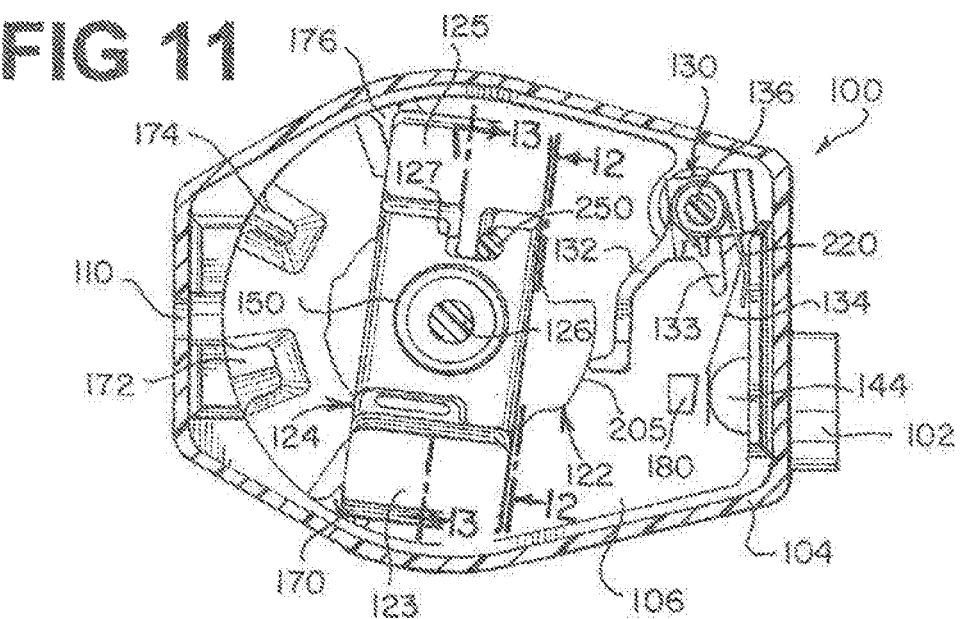
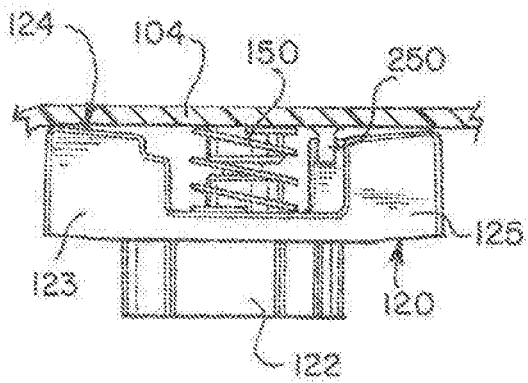

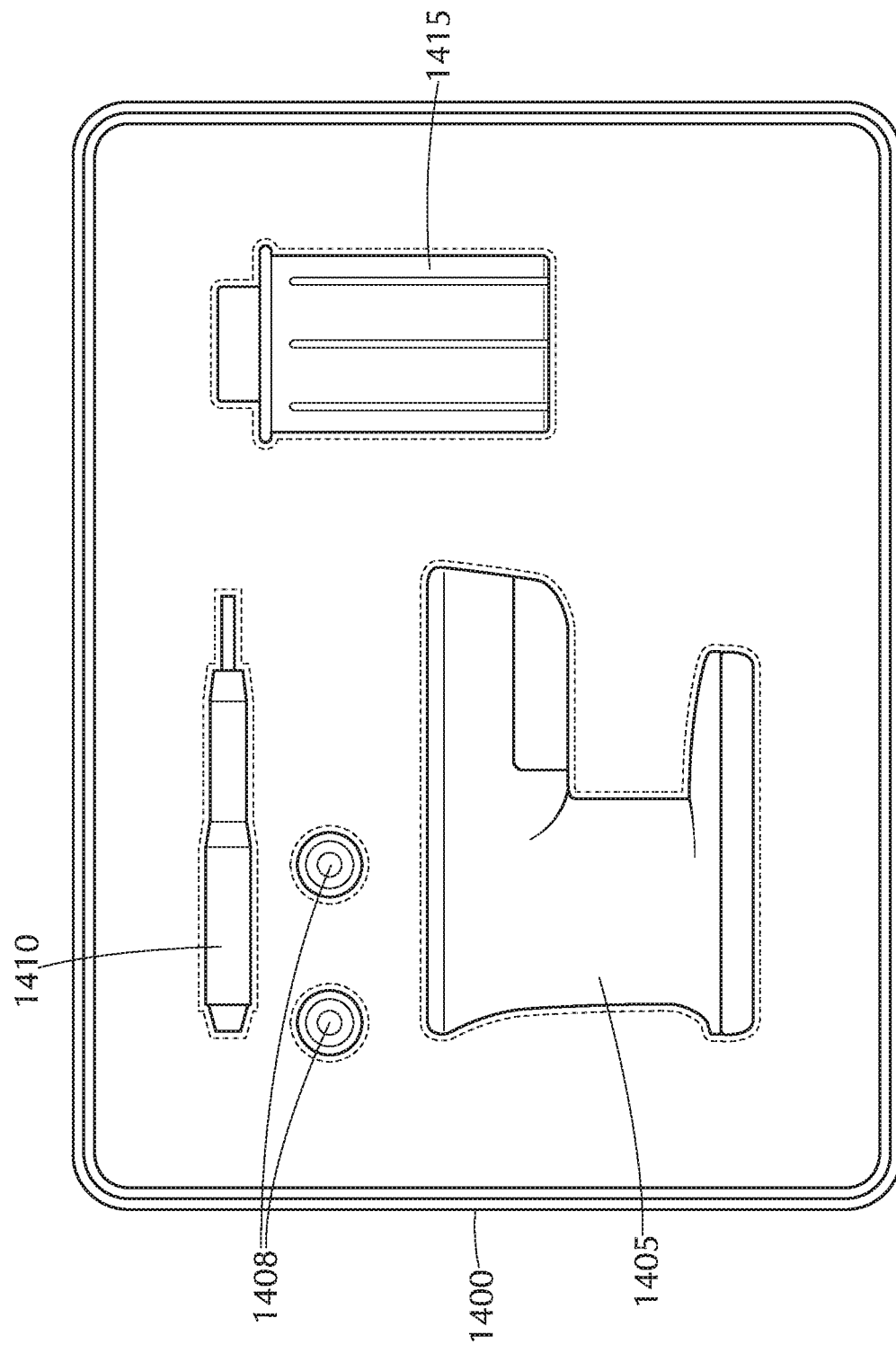

IMPLANTABLE BODILY FLUID DRAINAGE VALVE WITH MAGNETIC FIELD RESISTANCE ENGAGEMENT CONFIRMATION

BACKGROUND OF THE INVENTION

Field of the Invention

The present invention relates to a system and method for an implantable drainage valve for drainage of a bodily fluid (e.g., cerebrospinal fluid). In particular, the present inventive system and method is directed to verifying whether a mechanical feature in the valve for resisting changes to performance setting when exposed to magnetic fields is properly engaged. For example, magnetic fields generated while undergoing Magnetic Resonance Imaging (MRI) or other foreign magnetic fields generated by common household magnets (e.g., refrigerator magnets or electronic notebook covers.

Description of Related Art

Hydrocephalus is the accumulation of cerebrospinal fluid in the brain, resulting from increased production, or more commonly, pathway obstruction or decreased absorption of the fluid. Cerebrospinal fluid (CSF) shunts have been used for decades for the treatment of hydrocephalus. A CSF shunt involves establishing an accessory pathway for the movement of CSF to bypass an obstruction of the natural pathways.

The shunt is positioned to enable the CSF to be drained from the cerebral ventricles or sub-arachnoid spaces into another absorption site (e.g., the right atrium of the heart or the peritoneal cavity) through a system of small catheters. A regulatory device, such as a valve, may be inserted into the pathway of the catheters. In general, the valve keeps the CSF flowing away from the brain and moderates the pressure or flow rate. The drainage system using catheters and valves enables the excess CSF within the brain to be evacuated and, thereby, the pressure within the cranium to be reduced.

Some implantable valves are fixed pressure valves (i.e., monopressure valves) while others have adjustable or programmable settings. Programmable or adjustable implantable valves are desirable in that the valve pressure setting may be varied non-invasively via an external control device over the course of treatment without requiring explantation. One such conventional adjustable or programmable implantable valve using magnets is the CODMAN® HAKIM® Programmable Valve (CHPV), as disclosed in U.S. Pat. No. 4,595,390, which is assigned to DePuy Orthopedics, a J&J company related to that of the present assignee, and herein incorporated by reference in its entirety. Another programmable implantable drainage valve is the CODMAN® CERTAS® or CERTAS® Plus Programmable Valve, as disclosed in U.S. Pat. No. 8,322,365, also assigned to DePuy Orthopedics, a J&J company related to that of the present assignee, and which is herein incorporated by reference in its entirety. Medtronic also has a programmable implantable shunt valve Strata® controlled using magnets. The pressure setting in these aforementioned conventional programmable implantable valves may be non-invasively adjusted post implantation in the body using a rotating construct or rotor with at least one magnet.

Magnetic resonance imaging (MRI) is a medical procedure for examining internally one or more parts, organs or other sites of the body exposed to powerful magnetic fields (typically at approximately 3.0 Tesla magnetic exposure levels). However, due to the presence of the magnets in the programmable implantable drainage valve such systems are at high risk of malfunction or improper operation (e.g., unintentional changes in performance settings) when exposed to powerful magnetic fields, for example, during MRI procedures. Similar malfunction in operation of the valve may occur upon exposure to other magnets as well.

To avoid such risk, some conventional programmable implantable valves have been modified to include a locking, engagement or magnetic field resistance mechanism which, when functioning or operating properly, ensures that unintentional changes in the performance settings will not occur when the device is exposed to rogue or foreign magnets. However, if not properly locked or engaged the magnetic field resistance mechanism may not accomplish its intended functionality leaving the programmable implantable valve susceptible to possible change in parameter settings without advanced warning of such risk. Due to the possibility, albeit a relatively small probability, of non-engagement of the magnetic field mechanism (i.e., not properly seated or locked), the implantable bodily fluid drainage valve may not always be resistant to undesired changes in valve setting when exposed to foreign magnets.

It is therefore desirable to develop a system and method that confirms whether the magnetic field resistance mechanism is properly locked or engaged, and thus accomplishing its intended functionality of the valve resisting change in programmed valve settings when exposed to rouge or foreign magnets.

SUMMARY OF THE INVENTION

An aspect of the present invention is directed to a system and method that confirms whether the magnetic field resistance mechanism is properly locked or engaged, and thus accomplishing its intended functionality of the valve resisting change in programmed valve settings when exposed to rouge or foreign magnets.

Another aspect of the present invention relates to a method for verifying whether a magnetic field resistance mechanism is properly engaged in an implantable programmable bodily fluid drainage system comprising an implantable bodily fluid drainage valve having an adjustable valve unit including a rotating construct and a pair of primary magnetic elements for programming the adjustable valve unit to a desired valve setting. Using a toolset, a determination is made whether the magnetic field resistance mechanism is properly engaged. An alert is generated whether the magnetic field resistance mechanism is at least one of properly engaged or not properly engaged. In accordance with the present invention, the determination of whether the magnetic field resistance mechanism is properly engaged is based on: (i) a measured angular position of a detected one of the pair of primary magnetic elements relative to a direction of flow of fluid through the implantable bodily fluid drainage valve; and/or (ii) a measured distance separation between respective centers of the pair of primary magnetic elements.

In one particular aspect of the present invention, the implantable bodily fluid drainage valve includes a fixed reference magnet aligned with a marking on the implantable bodily fluid drainage valve denoting a direction of fluid flow therethrough and a center point midway between the pair of primary magnetic elements. The housing of the rotating construct comprises an upper casing having a plurality of downward projecting teeth in which the pair of primary magnetic elements are respectively located and a lower casing including a plurality of corresponding setting pockets for receiving the downward projecting teeth. Each of the setting pockets is bound on at least one side by a lock stop projecting upwardly from the lower casing towards the upper casing. In this particular aspect of the invention, the determination of whether the magnetic field resistance mechanism is properly engaged is based on the measured angular position of a detected one of the pair of primary magnetic elements relative to a direction of flow of fluid through the implantable bodily fluid drainage valve. Such determination includes the step of detecting using a sensor array in the toolset a magnetic field pattern produced by each of: (i) the fixed reference magnet; and (ii) the pair of primary magnetic elements. The center point midway between the detected pair of primary magnetic elements is then located. A direction of flow line is defined as a reference line intersecting with: (i) the arrow indicia denoting direction of flow of fluid through the implantable bodily fluid drainage valve; (ii) the located center point midway between the detected pair of primary magnetic elements; and (iii) the detected fixed reference magnet. Thereafter, a rotating construct vector is defined connecting centers of the detected pair of primary magnetic elements. A rotating construct angle is measured starting from the defined direction of flow line traveling in a counter-clockwise or clockwise direction until intersecting the rotating construct vector. Finally, the measured rotating construct angle is compared to a predetermined mechanical angular spacing for each of the setting pockets as stored in a memory device. If the measured rotating construct angle matches the predetermined mechanical angular spacing for any of the setting pockets then the magnetic field resistance mechanism is deemed properly engaged. Otherwise, if the measured rotating construct angle does not match the predetermined mechanical angular spacing for any of the setting pockets then the magnetic field resistance mechanism is deemed not to be properly engaged. That is, the magnetic field resistance mechanism is engaged when the plurality of downward projecting teeth are properly seated in the corresponding setting pockets, whereas the magnetic field resistance mechanism is not properly engaged when any of the plurality of downward projecting teeth are resting on one of the lock stops. The aforementioned determining step may be performed following programming of a valve setting of the implantable bodily fluid drainage valve and/or prior to a magnetic resonance imaging procedure.

In still another particular aspect of the present invention the implantable bodily fluid drainage valve includes a rotating construct rotatably mounted in a housing about an axis with a substantially cylindrical central part fixedly mounted on the axis. The rotating construct includes lateral branches on either side of the axis for moving parts each housing a respective one of the pair of primary magnetic elements with opposing faces of opposite polarity. A mating lead in element extends respectively from each of the moving parts. The moving parts are displacable linearly inside the rotating construct in a substantially radial direction thereof to actuate the mating lead in element in a circular succession of pockets defined radially inward along an outer perimeter of the substantially cylindrical central part. In this configuration, the mechanical resistance mechanism is engaged when the mating lead in element is seated in one of the pockets, whereas the magnetic field resistance mechanism is not engaged when the mating lead in element is resting along the outer perimeter of the substantially cylindrical central part between the pockets adjacent to one another. Moreover, in this configuration, the determination of whether the magnetic field resistance mechanism is properly engaged is based on the measured angular position of a detected one of the pair of primary magnetic elements relative to a direction of flow of fluid through the implantable bodily fluid drainage valve, as described above. Alternatively, in this configuration the determination of whether the magnetic field resistance mechanism is properly engaged may be based on the measured distance separation between respective centers of the pair of primary magnetic elements. This is accomplished by detecting a center of each of the pair primary magnetic elements. Then a distance separation between the detected center of each of the pair of primary magnets is calculated. The calculated distance separation is compared to a predetermined locking value. If the calculated distance separation is equal to the predetermined locking value, then the magnetic field resistance mechanism is deemed properly engaged. Otherwise, if the calculated distance separation is greater than the predetermined locking value, then the magnetic field resistance mechanism is deemed not to be properly engaged.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which:

FIG. 10 is a side cross-sectional view of the adjustable valve unit of FIG. 8 along lines 10-10 showing axial lifting of the rotatable construct;

FIG. 11 is a shallower partial top cross-sectional view of the adjustable valve unit of FIG. 6H showing the "virtual off" position in an unconstrained condition;

FIG. 12 is a side view along lines 12-12 of FIG. 11;

FIG. 14 is a perspective view of a tool set including an integrated locator/indicator tool, an adjustment tool and a screwdriver;

DETAILED DESCRIPTION OF THE INVENTION

Figure 1:
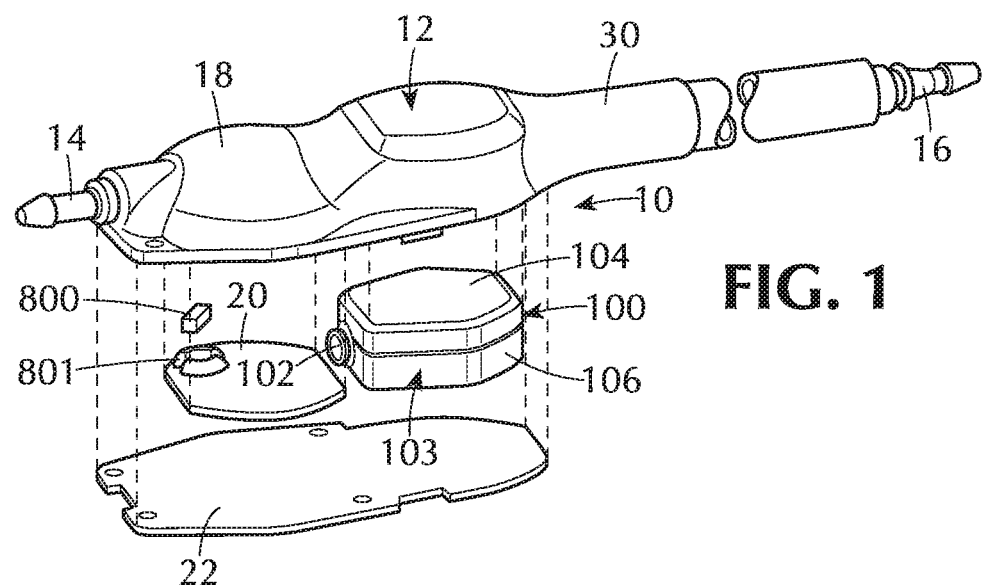
FIG. 1 is a schematic perspective exploded view of a programmable valve device having an adjustable valve unit.

FIG. 1 illustrates a prior art programmable shunt valve device 10 having a shunt housing 12, preferably formed of a translucent material such as silicone, with proximal connector 14 and distal connector 16. A ventricular catheter or other proximal catheter is connectable to connector 14 to bring fluid into shunt housing 12. Fluid passes into sampling or pumping chamber 18 and then through a valve mechanism in inlet 102 into adjustable valve unit 100, which is shown and described in more detail below in relation to FIGS. 2-13A. Valve unit 100, FIG. 1, includes a casing 103 formed as upper casing 104 and lower casing 106 which are joined by sonic welding in this construction. A needle guard 20, preferably formed of a rigid polymeric material, and lower casing 106 are secured within housing 12 by a backing plate 22, preferably formed of silicone reinforced with a polymeric mesh, which is bonded to housing 12 by a medical grade epoxy. A fixed reference magnet 800, as described in detail further below, is preferably seated in a bump or projection 801 on the needle guard 20.

When fluid pressure at inlet 102 exceeds a selected pressure setting within valve unit 100, fluid is admitted past a valve mechanism and then flows through valve unit outlet 110 into passage 30 of housing 12. Ultimately, fluid exits from housing 12 through distal connector 16 into a peritoneal catheter or other distal catheter.

Figure 2:
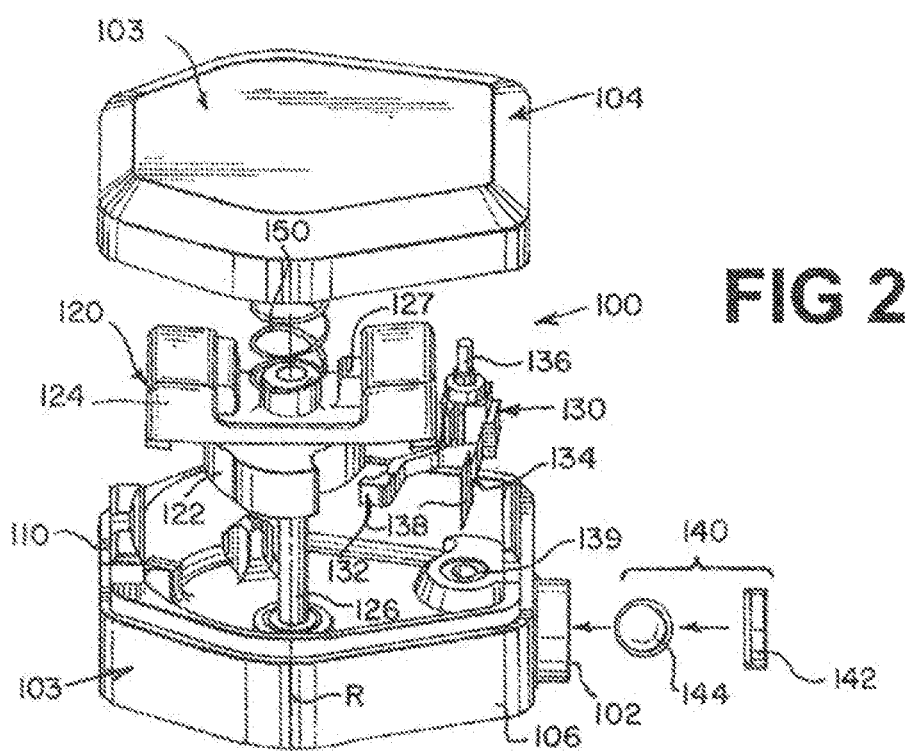
FIG. 2 is an exploded perspective view of the adjustable valve unit of FIG. 1.

Valve unit 100, FIG. 2, includes a rotor 120, spring arm unit 130, valve mechanism 140, and a rotor retention spring 150. Rotor 120, also referred to as a rotating construct, is formed of a lower cam structure 122 having a plurality of radially flat cam surfaces, as shown and described in more detail below, and an upper, magnet housing 124 carrying magnetic elements 123 and 125, N and S pole magnets, respectively. Housing 124 also defines a finger 127 which engages a stop in upper casing 104 when rotor 120 is moved to an unconstrained condition as described below. Rotor 120 rotates about axle 126 which defines a substantially fixed axis of rotation R at a first location in casing 103.

Preferably, rotor 120 is also capable of moving along the axis of rotation, in a translational motion, to an unconstrained condition when an adjuster tool is applied to it, as described in more detail below. Retention spring 150 biases rotor 120 to a downward, normally constrained condition. Preferably, spring 150 is a coil spring having sufficient bias to resist the effect of gravity, regardless of the position of the valve unit, and to resist magnetic or ferrous objects, such as magnets in an indicator tool described in more detail below. However, spring 150 is insufficient to resist the effects of an adjustment tool, also described below. Lower cam section 122 has a sufficient height to ensure that cam follower 132 remains in contact with a cam surface in both the constrained and unconstrained conditions.

Spring arm unit 130 includes cam follower 132, a resilient spring element 134, and upper and lower axles 136 and 138 at a second location in casing 103. Axle 138 turns about a bearing 139 formed of a low-friction, hard material such as synthetic ruby. It is desirable for casing 103, rotor 120 and spring arm unit 130 to be formed of polyethersulfone, while all spring components are formed of medical grade non-ferromagnetic stainless steel.

Valve mechanism 140 includes seat 142 and movable valve member 144. Preferably, seat 142 and valve member 144, such as a ball, are formed of the same non-ferromagnetic material such as synthetic ruby. In other constructions, the movable valve member may be a disc, a cone, or other type of plug. A spherical ball is currently preferred because that shape enables tight, precise tolerances, assembly and control relative to the valve seat. Also, the position of the seat within a port can be adjusted during assembly of the valve unit to alter the actual performance value achieved at each setting, using a force versus displacement relationship. First, a mandrel checks the position of the ball, and the seat is inserted to an estimated desirable location within the port. Ball displacement is tested at one or more settings to confirm that desired performance will be achieved.

Figure 3:
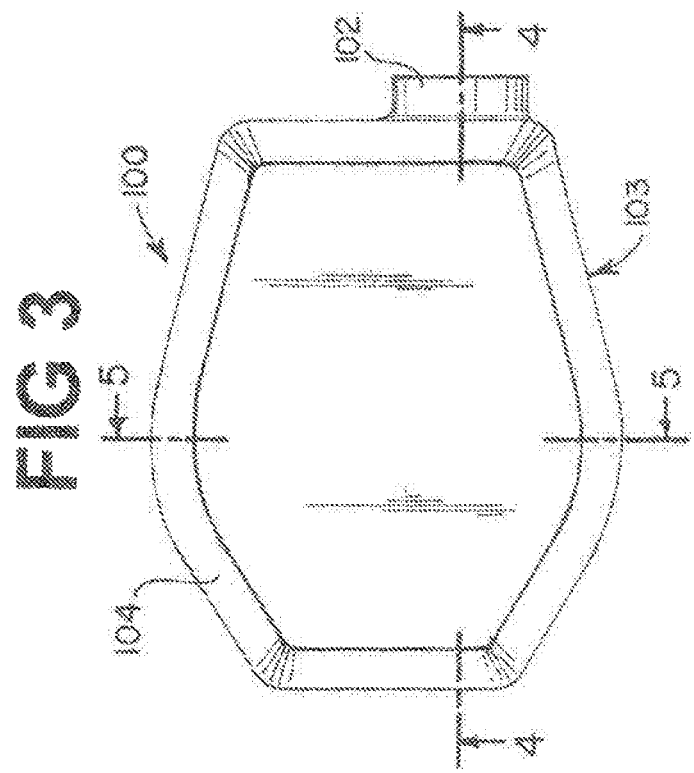
FIG. 3 is a top view of the adjustable valve unit of FIG. 2.

Valve unit 100 is shown assembled in FIGS. 3-5 and positioned at a second pressure setting, as described in more detail below. Rotor housing 124 carries downwardly projecting teeth 160 and 162 with cooperate with four lock stops projecting upwardly from lower casing 106 in this construction. Lock stop 172 is shown in partial cross-section in FIG. 4 and lock stops 170 and 176 are visible in FIG. 5. Preferably, the lower surfaces of rotor teeth 160 and 162 are rounded and the upper surfaces of casing lock stops 170, 172, 174 and 176 each have a plurality of facets to create a chisel-like, lead-in topography which encourages the rotor teeth to return to a constrained position, as illustrated in the side view in FIG. 4A. However, the vertical surfaces of teeth 160, 162 and of stops 170-176 abut when engaged and do not "lead out", that is, relative translational movement is discouraged, once again illustrated in FIG. 4A. Pure vertical lift must be provided by an adjustment tool, as described in more detail below, to overcome the tooth-to-stop abutment and change the performance setting.

Figure 4:
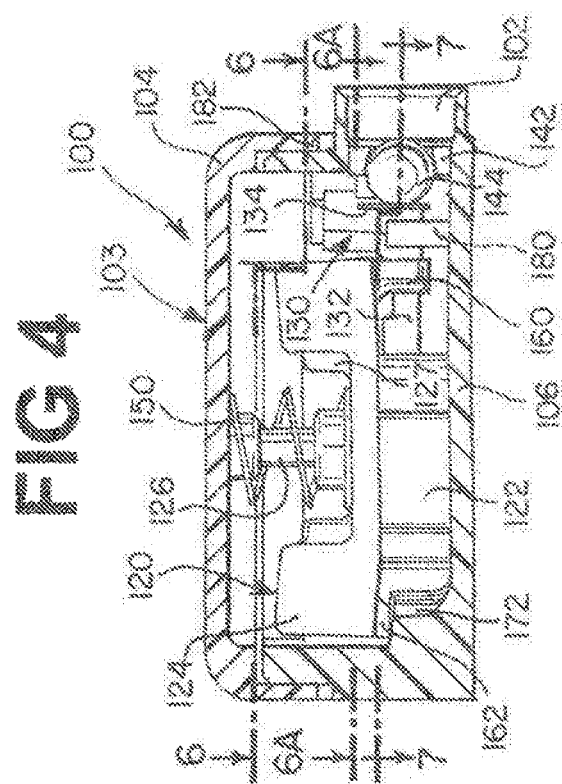
FIG. 4 is a side cross-sectional view of the adjustable valve unit of FIG. 3 along lines 4-4.
Figure 4A:
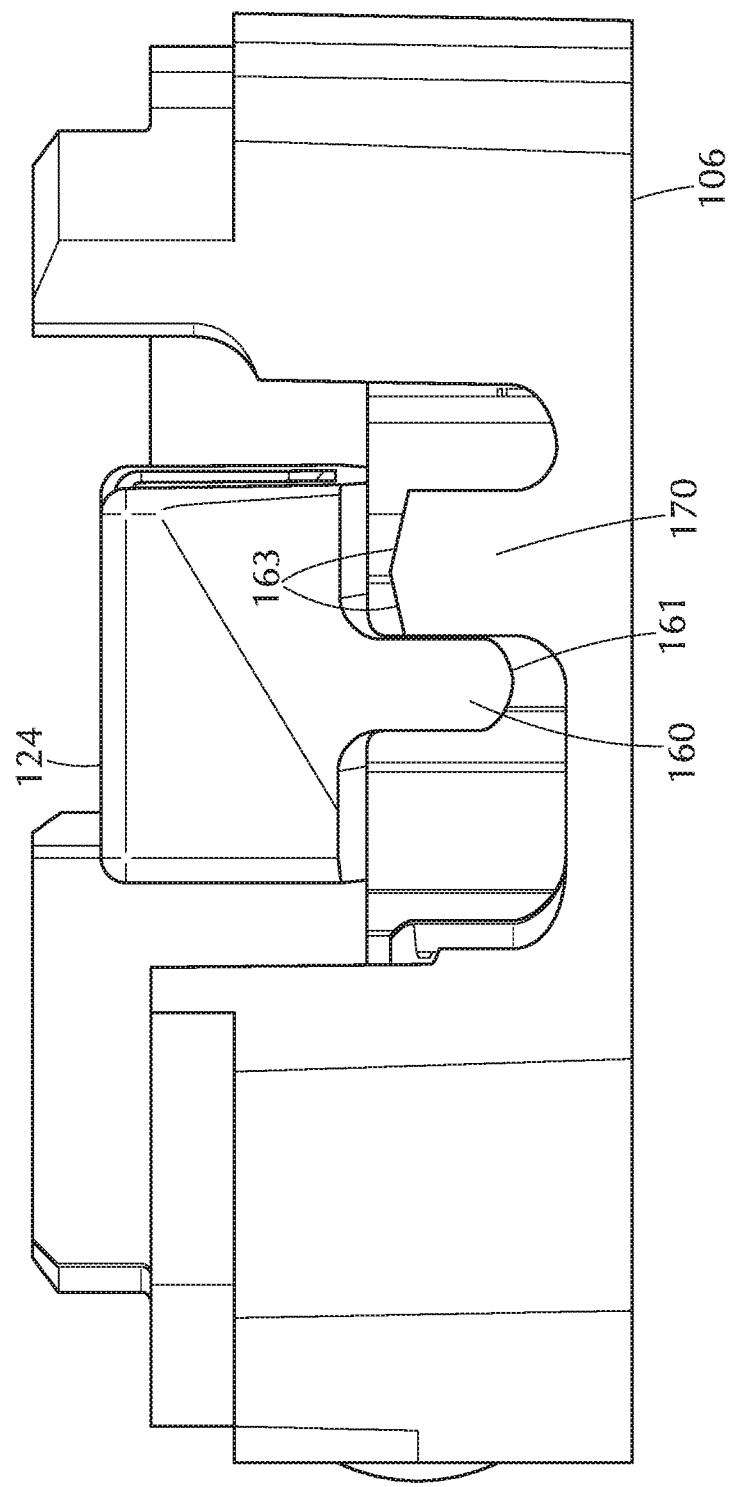
FIG. 4A is a side view of a single rotor tooth in engagement with a single lock stop.
Figure 5:
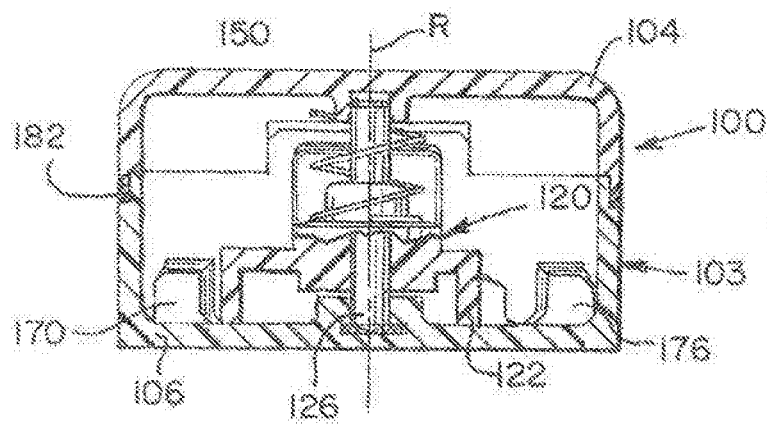
FIG. 5 is a cross-sectional view of the adjustable valve unit of FIG. 3 along lines 5-5.

A limiter 180, FIG. 4, restricts travel of spring 134 away from seat 142 so that ball 144 does not become misaligned or dislodged relative to seat 142. A gasket 182 of epoxy is shown in FIGS. 4 & 5 as an optional, redundant seal between upper casing 104 and lower casing 106 in this construction.

Figure 6:
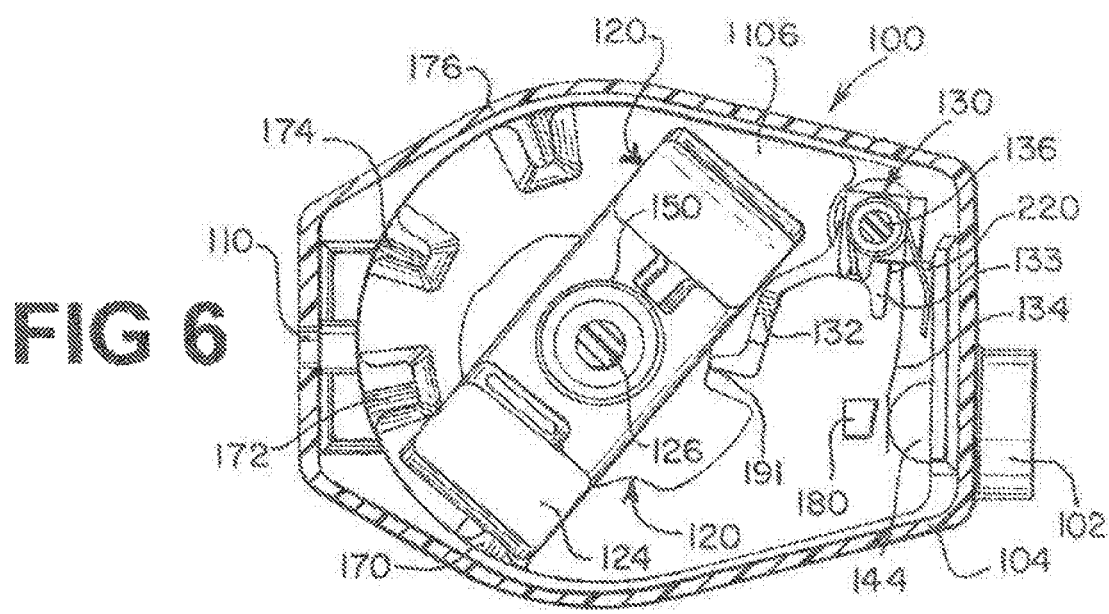
FIG. 6 is a partial cross-sectional view of the adjustable valve unit of FIG. 4 approximately along lines 6-6 at a first pressure setting.
Figure 6A:
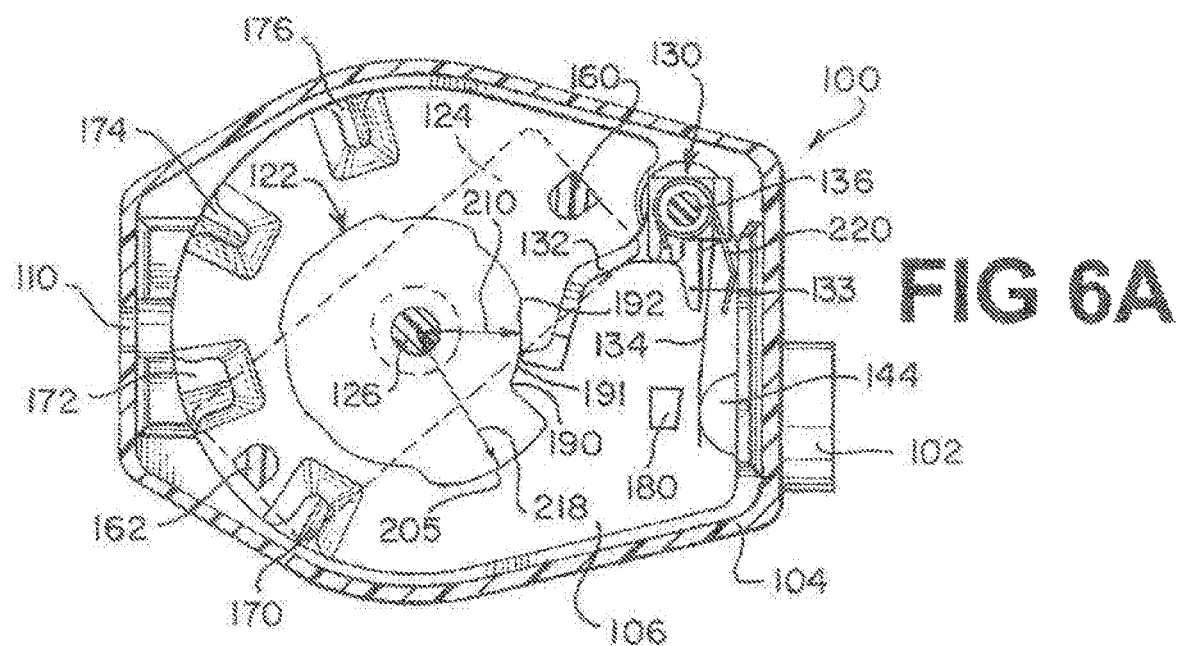
FIG. 6A is a deeper cross-sectional view of the adjustable valve unit of FIG. 4 approximately along lines 6A-6A at a first pressure setting.
Figure 7:
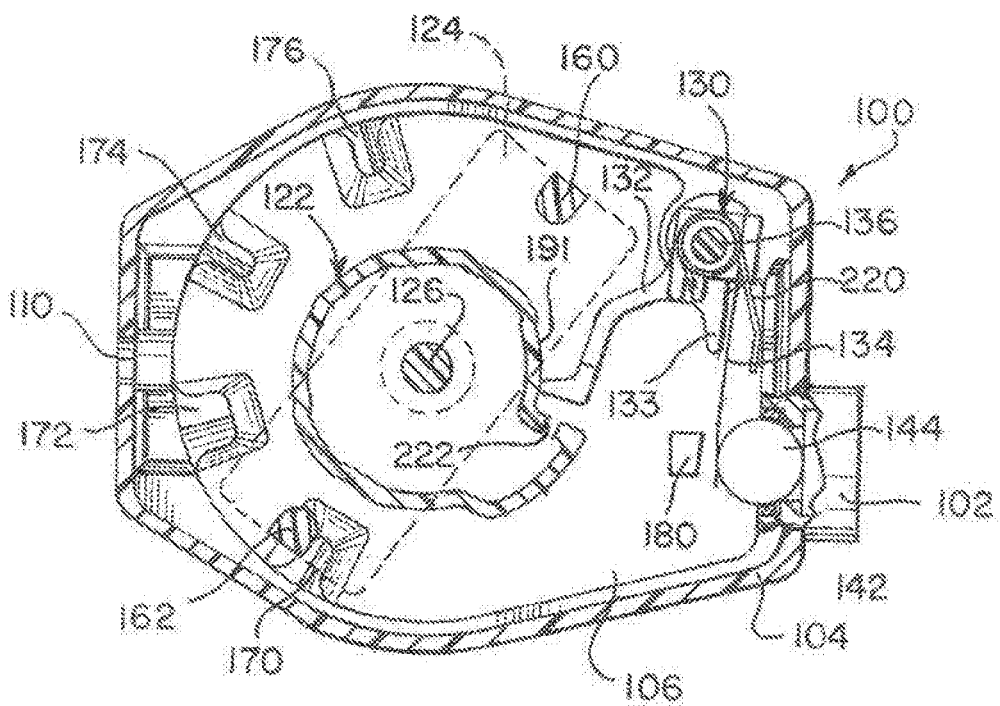
FIG. 7 is a deeper cross-sectional view of the adjustable valve unit of FIG. 4 approximately along lines 7-7.
Figure 8:
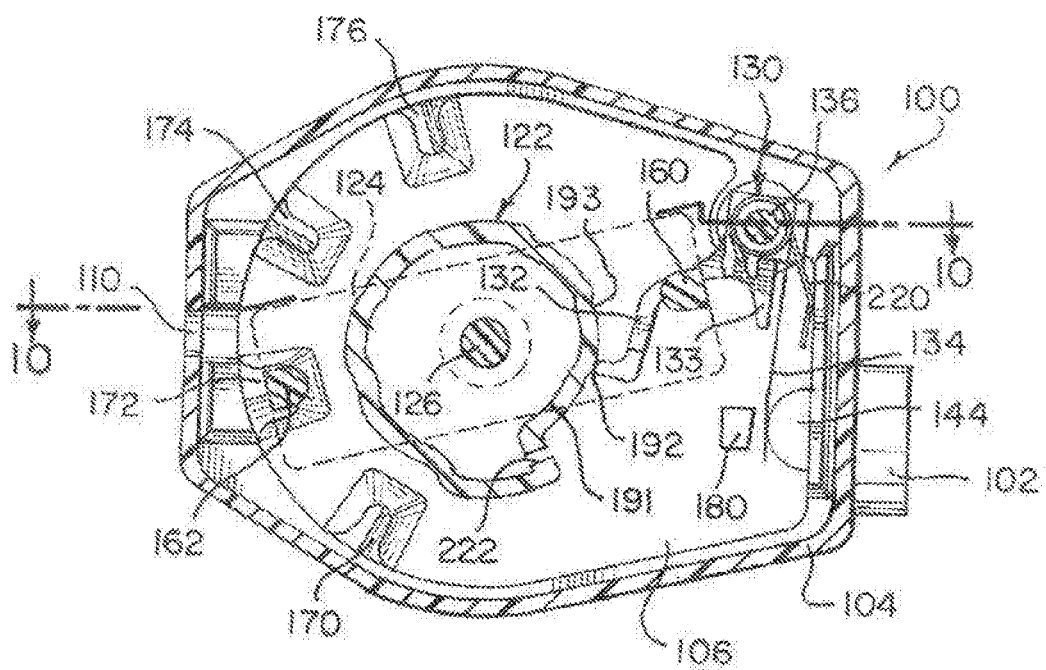
FIG. 8 is a cross-sectional view of the adjustable valve unit of FIG. 7 showing the transition to a different pressure setting.

The operation of valve unit 100 is illustrated in FIGS. 6-8 in relation to valve unit 100, with identical reference numerals identifying identical components and features. Not all such components and features are labelled in each drawing for the sake of visual clarity. FIGS. 6 & 6A show different levels of top partial cross-sectional views for valve unit 100 at a first pressure setting. Cam follower 132 slidably contacts only a first cam surface 191, which has an arc length bounded by points 190 and 192, because rotor housing tooth 162 is captured between casing lock stops 170 and 172 in the normal, constrained condition. First cam surface 191 has a first, preferably shortest radial distance 210 relative to the axis of rotation of rotor 120. By comparison, outermost cam surface 205 has a greatest radial distance 218. An optional torsion spring 220 is shown in greater detail in FIG. 9.

When rotor 120 is translated upwardly by magnets using an adjustment tool rotor tooth 162 is lifted so that subsequent clockwise or counter-clockwise rotation of the adjustment tool rotates tooth 162 up and over casing lock stop 172. After the adjustment tool is removed and when the second pressure setting has been selected as shown in FIG. 6B, rotor 120 is biased downwardly by spring 150, FIGS. 2, 4 & 5.

Figure 6B:
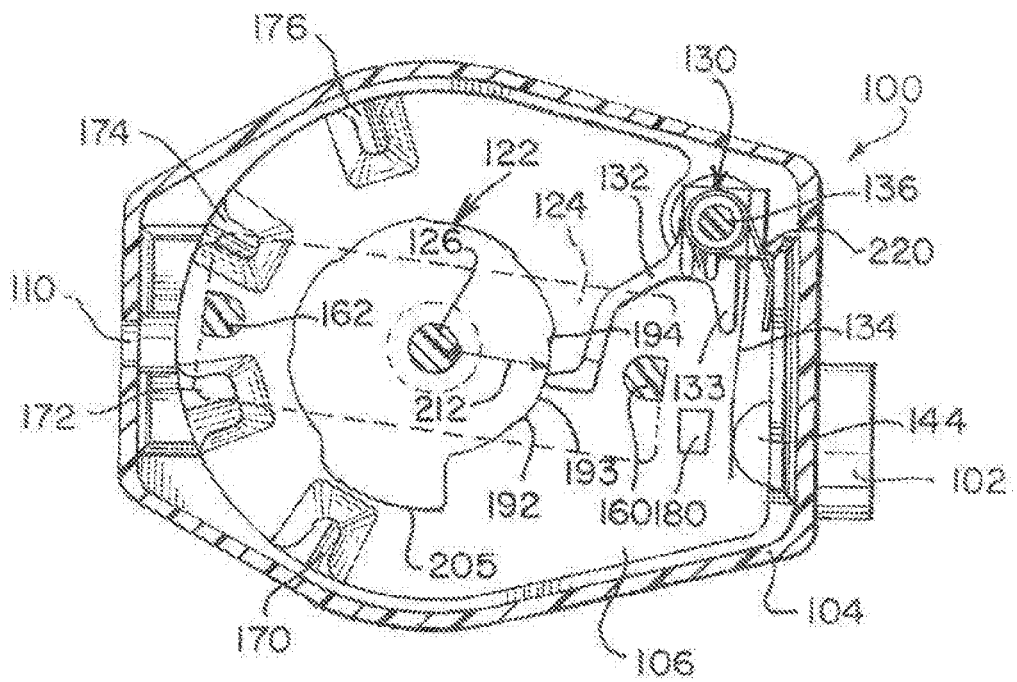
FIGS. 6B-6H are partial cross-sectional view of the adjustable valve unit of FIG. 4 at different, successive pressure settings.

Rotor tooth 160 is illustrated as not being in contact with any stop in FIGS. 4 & 6B, for example, because in the constrained condition rotor tooth 162 is now captured between a pair of lock stops 172 and 174, FIG. 6B, which is sufficient to prevent rotation of rotor 120 relative to the cam follower 132 beyond points 192 and 194 on the cam structure of rotor 120. Points 192 and 194 represent a second arc length for second cam surface 193. Surface 193 is at a second radial distance 212 which is greater than distance 210 and is less than distance 218, FIGS. 6A & 6H. The arc length of second cam surface 193, FIG. 6B, can be the same or different than the arc length of first cam surface 191 but, preferably, is substantially the same length.

The outward radial motion of cam follower 132 as it slidably travels from first cam surface 191, FIG. 6A, to second cam surface 193, FIG. 6B, increases the biasing force by valve spring 134 on ball 144 as increased torque is applied by cam follower 132 to the remainder of spring arm unit 130. Improved precision in pressure control is achieved by having a stiff cam follower 132 in contact with the selected cam surface and a flexible element, spring 134, in contact with the valve ball 144. The enhanced result is opening of the ball 144 from the valve seat 142 by requiring only the resilient spring element 134 to bend, which provides a constant spring force to the ball 144. The opening pressure, and overall valve performance, is not reliant on axial pivoting of the spring arm unit 130.

Figure 6C:
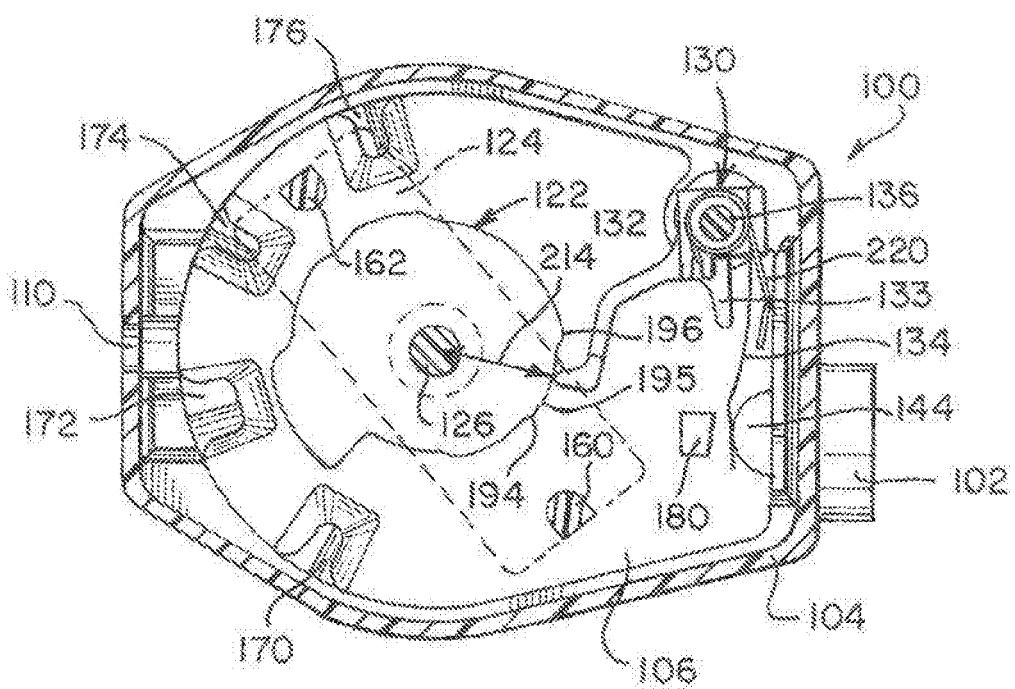
Figure 6D:
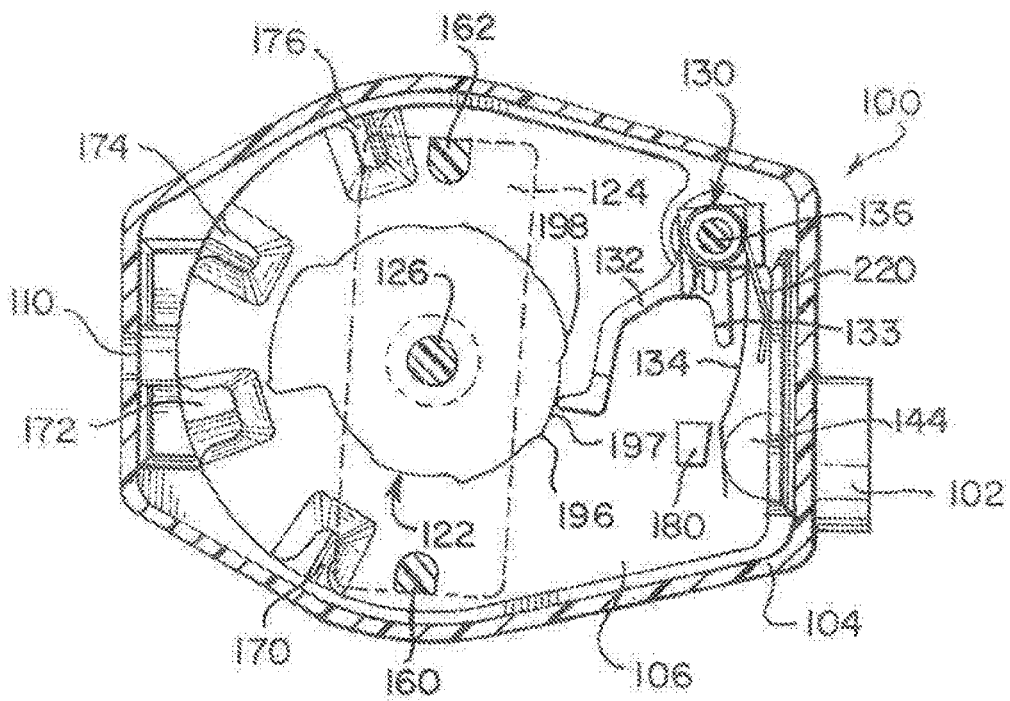

A third opening pressure setting is shown in FIG. 6C with rotor tooth 162 positioned between casing stops 174 and 176 such that cam follower 132 experiences only third cam surface 195 between points 194 and 196 at a third radial distance 214. To achieve a fourth pressure setting, FIG. 6D, both rotor teeth 160 and 162 are utilized relative to casing stops 170 and 176, respectively. Cam follower 132 is restricted thereby to fourth cam surface 197 between points 196 and 198.

Figure 6E:
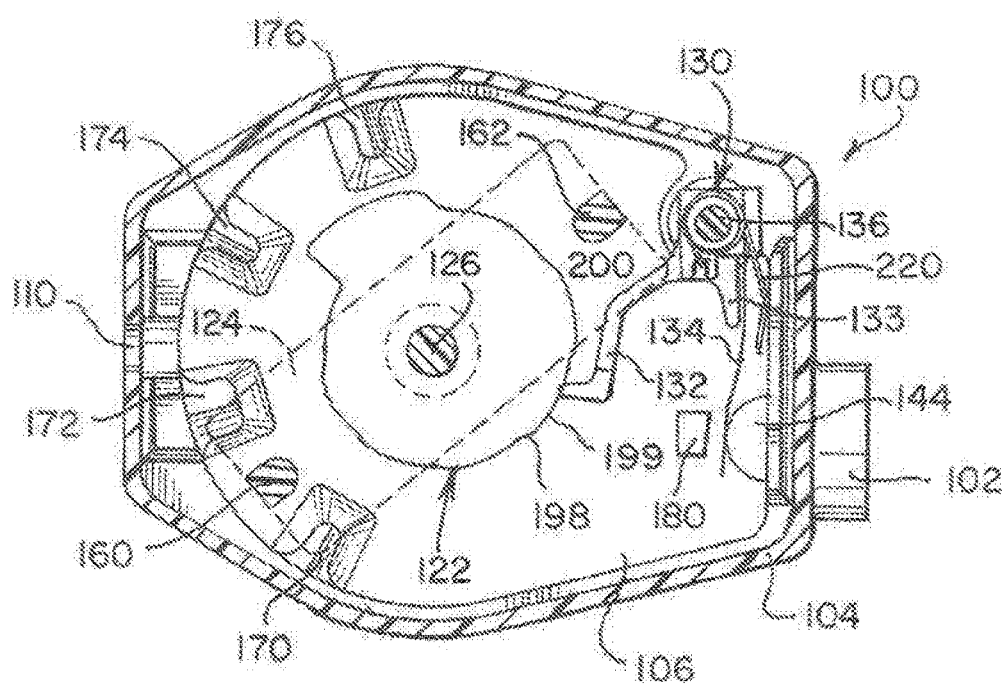
Figure 6F:
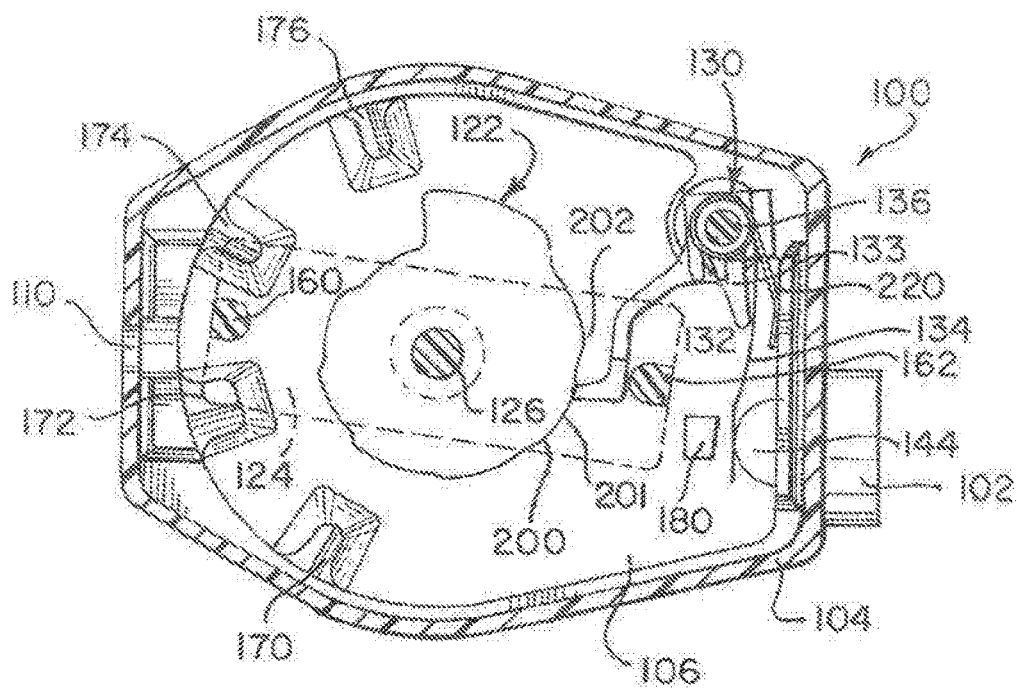
Figure 6G:
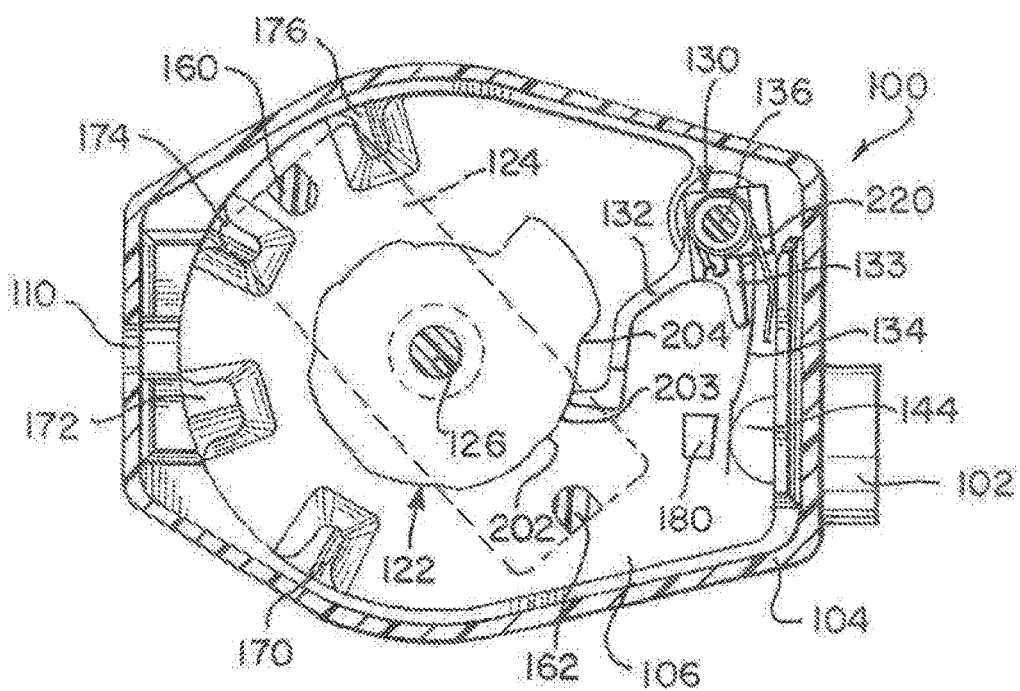

Fifth through seventh pressure settings are illustrated in FIGS. 6E-6G as rotor tooth 160 is successively captured between casing lock stop pairs 170-172, 172-174, and 174-176, respectively. Cam follower 132 is restricted thereby to fifth cam surface 199 between points 198 and 200, FIG. 6E, sixth cam surface 201 between points 200 and 202, FIG. 6F, and seventh cam surface 203 between points 202 and 204, FIG. 6G.

Preferred opening pressure settings currently range from approximately 30 mm to 210 mm water (294 Pa to 2,059 Pa) in seven increments of 30 mm (294 Pa), with a final, "virtual off" setting described in more detail below. Preferably, each valve unit is calibrated and tested at the time of manufacture at one or more flow rates. Actual opening pressure for each setting tends to vary according to flow rate, typically measured in milliliters per hour. Also, when tested with a 120 cm long distal catheter having an inner diameter of 1 mm, the average opening pressure typically will increase by 9 mm water or more at flow rates of 5 ml/h or more.

Figure 6H:
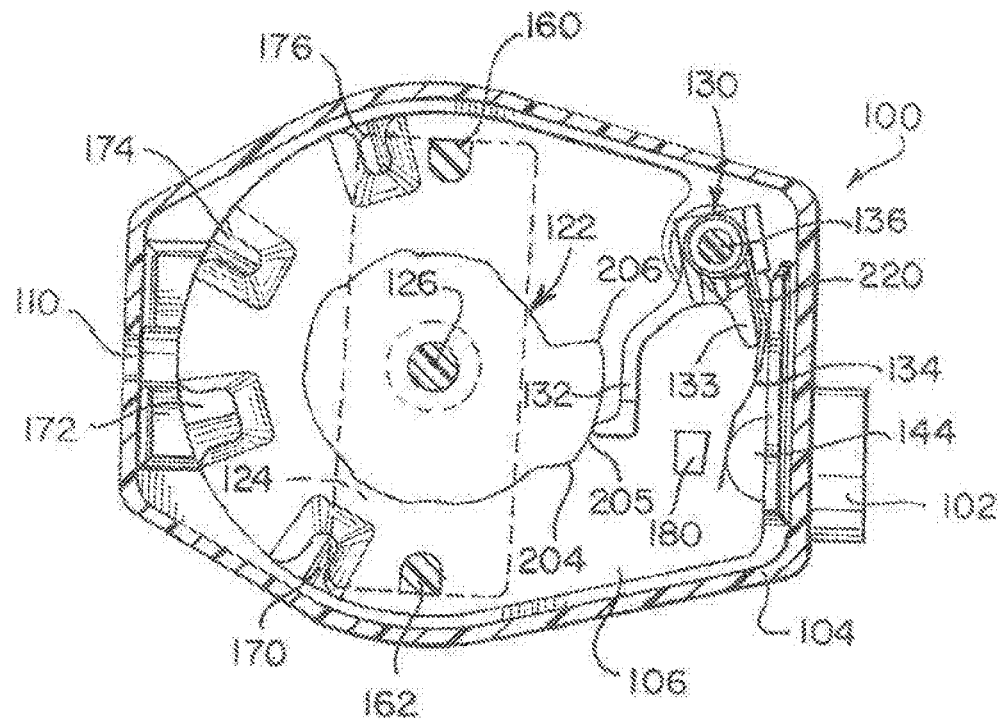

The final setting, FIG. 6H, of approximately at least 400 mm water (3,920 Pa) minimizes flow as a "virtual off" setting, that is, as substantially closed. This final setting is achieved by exposing cam follower 132 to outermost cam surface 205, defined by points 204 and 206, having greatest radial distance 218. This greatest cam setting forces stiffener element 133 of spring arm unit 130 against valve spring 134 to shorten its active, effective length and thereby dramatically increase the biasing force applied against ball 144. The final opening pressure is increased by more than fifty percent over the prior setting. In other constructions, a stiffener element is forced against a valve spring during two or more final cam settings at desired pressure increments.

Figure 9:
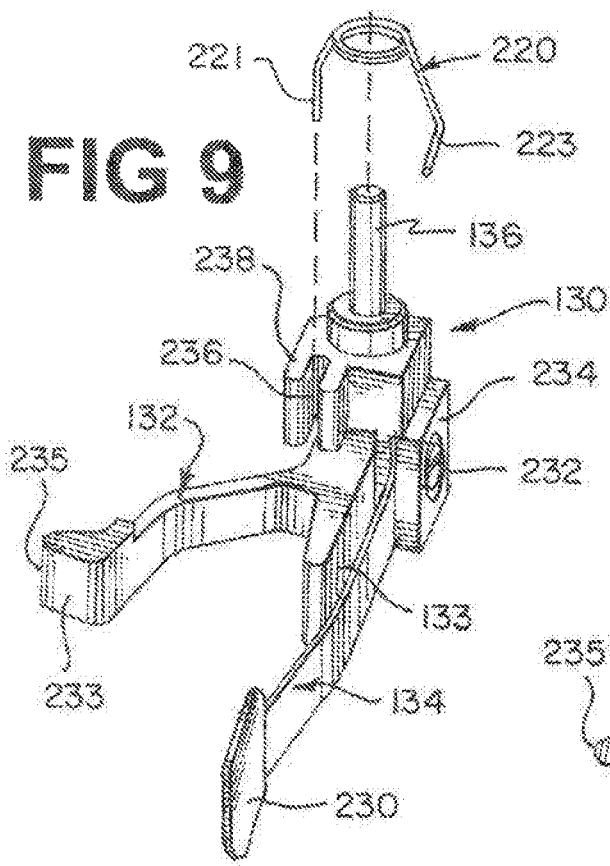
FIG. 9 is a perspective view of the spring arm unit with optional torsion spring.
Figure 9A:
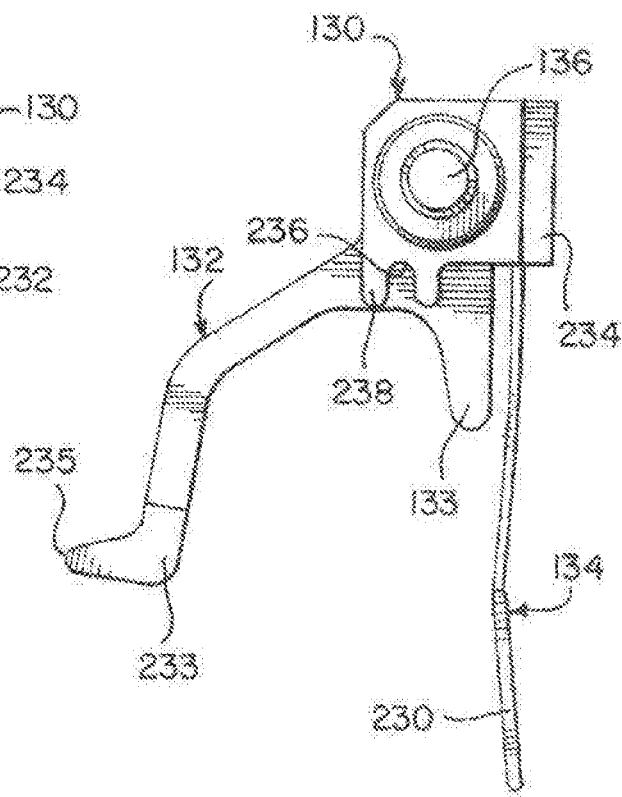
FIG. 9A is a top plan view of the element of FIG. 9.

Spring arm unit 130 is shown in greater detail in FIGS. 9 and 9A with cam follower 132, stiffener element 133, and valve spring 134. Cam follower 132 terminates in a triangular head 233 with rounded or chamfered edges, one of which serves as a bearing surface 235. In a preferred construction, spring element 134 is formed from stainless steel having a thickness of 0.020 inches and terminates in an enlarged pad 230 for contacting the valve ball or other movable valve member. In one construction, spring element 134 is attached to the remainder of spring arm unit 130 by a post 232 and rivet 234 which are secured by ultrasonic welding. Torsion spring 220 has a first leg 221 which is retained in recess 236 of projection 238. Second spring leg 223 rests against an inner surface of the casing.

Use of torsion spring 220 is optional, and is possible because only spring element 134 contacts the movable valve member. As a result, additional spring force from torsion spring 220 can be utilized to force bearing surface 235 of cam follower 132 against a cam surface of the rotor. This biasing force provided by torsion spring 220 augments rotational position of the spring arm reflective of the intended cam displacement without otherwise impacting the force applied to the ball or other movable valve member. This provides for a more accurate and repeatable opening pressure and a more manufacturable and robust design as it reduces the need to maintain minimal friction such as when the valve spring element solely provides the force needed to maintain the cam follower on the cam surface.

The position of the components and features within valve unit 100 at the first pressure setting shown in FIG. 6A is illustrated at a deeper partial cross-sectional view in FIG. 7. Opening 222 into the lower cam portion of rotor 120 inhibits negative pressure from developing under rotor 120, that is, opening 222 ensures pressure equalization as cerebrospinal fluid passes through valve unit 100.

The transition from the first pressure setting to the second pressure setting is illustrated in FIGS. 8 & 10 as rotor 120 is translated upwardly by magnetic attraction with an adjustment tool so that rotor tooth 162 is able to clear casing lock stop 172. Cam follower 132 is shown in FIG. 8. 8 at point 192 passing from first cam surface 191 to second cam surface 193. Lower cam section 122 has a sufficient height relative to cam follower bearing surface 235 to ensure that cam follower 132 remains in contact with a cam surface of cam portion 122 in both the constrained and unconstrained conditions. Rotor retention spring 150, FIG. 10, has been compressed, its biasing force being overcome by magnetic attraction between rotor 120 and the adjustment tool while it is positioned over valve unit 100. Also illustrated in FIG. 10 are upper and lower synthetic ruby bearings 242 and 139 for upper and lower axles 136 and 138, respectively, of spring arm unit 130. Synthetic ruby bearing 240 rotatably supports rotor axle 126.

The position of the components and features within valve unit 100 at the final, "virtual off" or substantially closed setting shown in FIG. 6H is depicted at a shallower cross-sectional view in FIG. 11 in an unconstrained condition. Further clockwise rotation of rotor 120 is prevented by rotation stop or limiter 250 which projects downwardly from upper casing 104 to contact finger 127. Rotation stop 250 contacts the opposite surface of finger 127 when rotor 120 is turned fully counter-clockwise in an unconstrained condition. The actual position of rotation stop 250 may be shifted to the right of the position shown in FIG. 11 so that cam follower 132 is able to track nearly the entire portion of cam surface 205. Preferably, one side of stop 250 prevents rotor movement from the lowest setting directly to the highest setting, and also prevents the cam follower from touching the cam projection for the highest setting when the rotor is at its lowest setting. The other side of stop 250 prevents movement from the highest setting directly to the lowest setting. A side, partial cross-sectional view of rotation stop 250 blocking rotor housing 124, as well as spring 150 compressed between rotor 120 and upper casing 104, is shown in FIG. 12 for this unconstrained condition.

Figure 13:
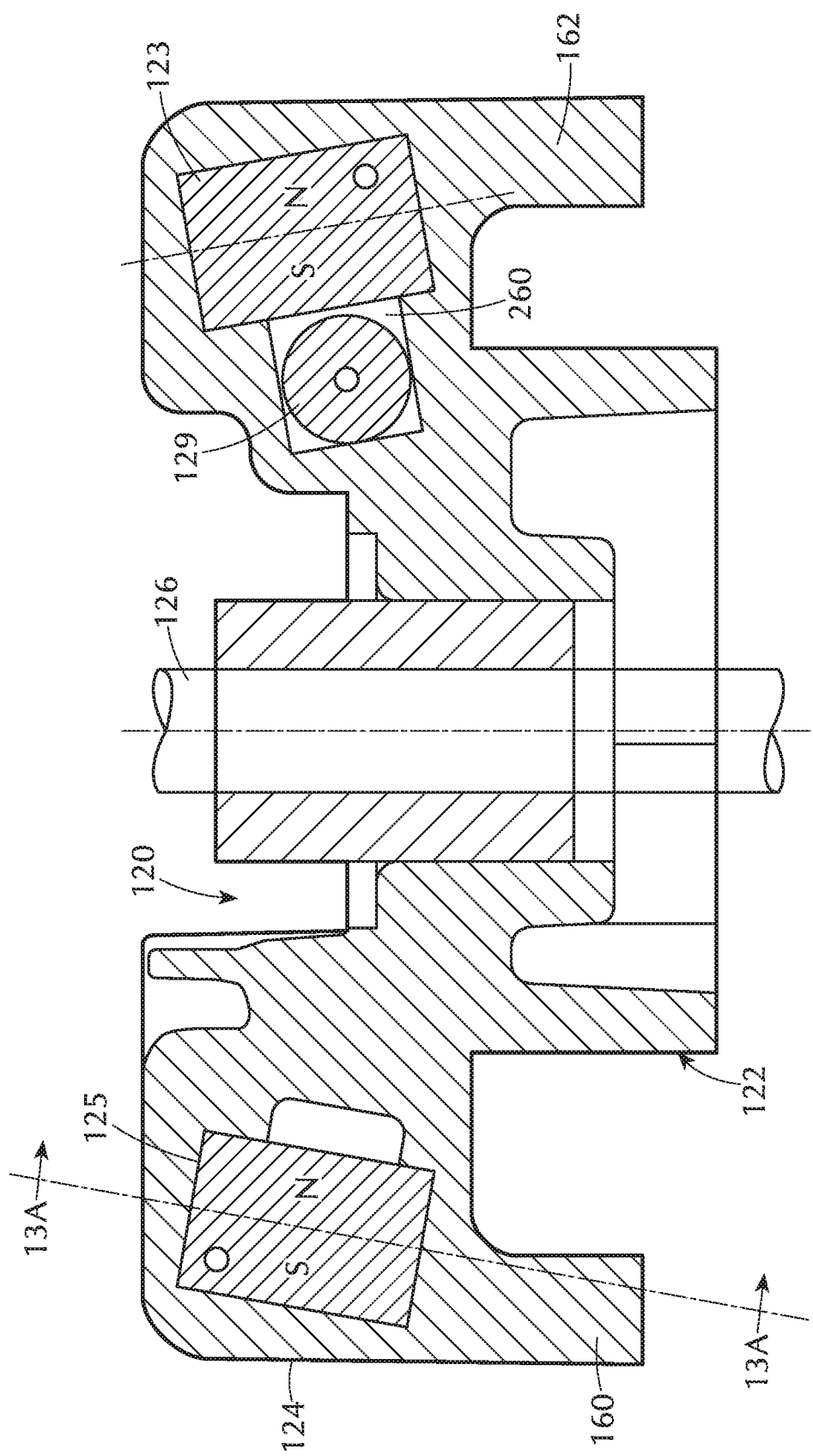
FIG. 13 is a side cross-sectional view along lines 13-13 of FIG. 11.
Figure 13A:
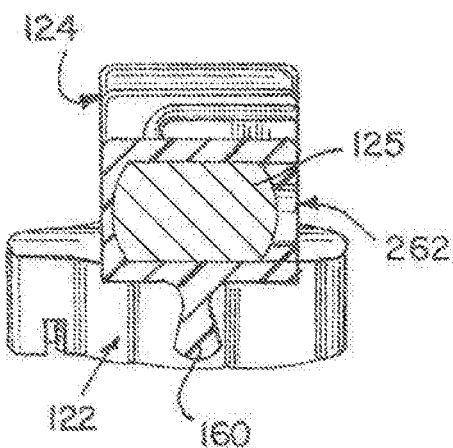
FIG. 13A is a partial cross-sectional view along lines 13A-13A of FIG. 13.

Further detailed views of selected features and components of rotor 120 in one construction are illustrated in FIGS. 13 & 13A. In particular, the housing portion 124 is shown as integral with cam portion 122. Pocket cavity 260, FIG. 13, contains magnet 123 and tantalum reference ball 129 which is readily visible during imaging of the valve unit 100 after implantation in a patient to confirm the actual pressure setting. Pocket cavity 262 holds magnet 125. A partial end view of housing portion 124 through magnet 125, pocket 262 and rotor tooth 160 is provided in FIG. 13A.

It is therefore the particular design of the abutting rotor-tooth-to-lock-stop vertical surfaces requiring purely vertical lift by an adjustment tool to overcome the rotor-tooth-to-lock-stop abutment in order to change the pressure setting that provides the resistance to change of valve settings in the presence of a foreign magnet. The rotor-tooth-to-lock-stop abutment mechanically prevents rotational movement from a given performance setting as the vertical surfaces provide no lead in to facilitate travel up and over the casing stops. Axial movement is restricted due to the orientation of the rotating construct magnets inducing a combined attraction and repulsion when interacting with a strong north or south magnet. Furthermore, the interference between the axle and the bushing surface of the rotating construct mechanically limit tilt associated with attraction/repulsion to an external magnetic field.

However, it is only when the downward projecting teeth 160, 162 of the rotor housing 124 are properly locked, engaged or seated in corresponding setting pockets 171, 171', 171", 171' defined by at least one of the lock stops 170, 172, 174, 176 projecting upwardly from the lower casing 106 that the programmable implantable bodily fluid drainage valve is resistant to magnetic fields from foreign magnets. The device has been tested to be 100% resistant to change of valve settings at least for magnetic fields up to approximately 3T so long as the magnetic field resistance mechanism is properly engaged. FIGS. 6A-6H depict proper engagement of the magnetic field resistance mechanism for each of the 8 valve settings. During programming or adjustment of the valve it is mechanically possible for the downward projecting teeth 160, 162 when vertically lowered to undesirably rest on top of one of the lock stops 170, 172, 174, 176. FIG. 8 illustrates just such an example with tooth 162 resting on top of lock stop 172. When one of the teeth 160, 162 is resting on top of a lock stop 170,172, 174, 176 (i.e., not properly seated or engaged in the respective setting pockets defined between adjacent lock stops) the programmable implantable bodily fluid drainage valve is at risk of possible unwanted change to the valve setting if exposed to a magnet. Heretofore, conventional programming valves are not able to verify whether the magnetic field mechanism is properly locked or engaged, that is whether teeth 160, 162 are properly seated in the setting pockets 171, 171', 171", 171'. It is therefore uncertain whether the valve would be resistant to possible change in setting when exposed to magnetic fields. To be certain, following exposure to a foreign magnet (e.g., after undergoing an MRI procedure), the programmed valve setting must once again be verified by medical personnel using the indicator tool from the associated toolset. Despite the relative small probability of the teeth not being properly seated, the possibility of a change in valve setting upon exposure of the valve to a foreign magnet is still particularly problematic since the implantable programmable bodily fluid drainage valve cannot be guaranteed as being resistant to magnetic fields within a predetermined range (up to approximately 3T).

The present inventive improved implantable valve drainage system eliminates this uncertainty by verifying, following programming of a valve setting or in advance of exposure to a foreign magnet, whether the downward projecting teeth 160, 162 are properly seated in the respective seating pockets 171, 171', 171", 171'. In essence, verifying whether the magnetic field resistance mechanism is properly locked or engaged to ensure that the valve setting does not change if the valve is exposed to a foreign magnet.

Figure 6I:
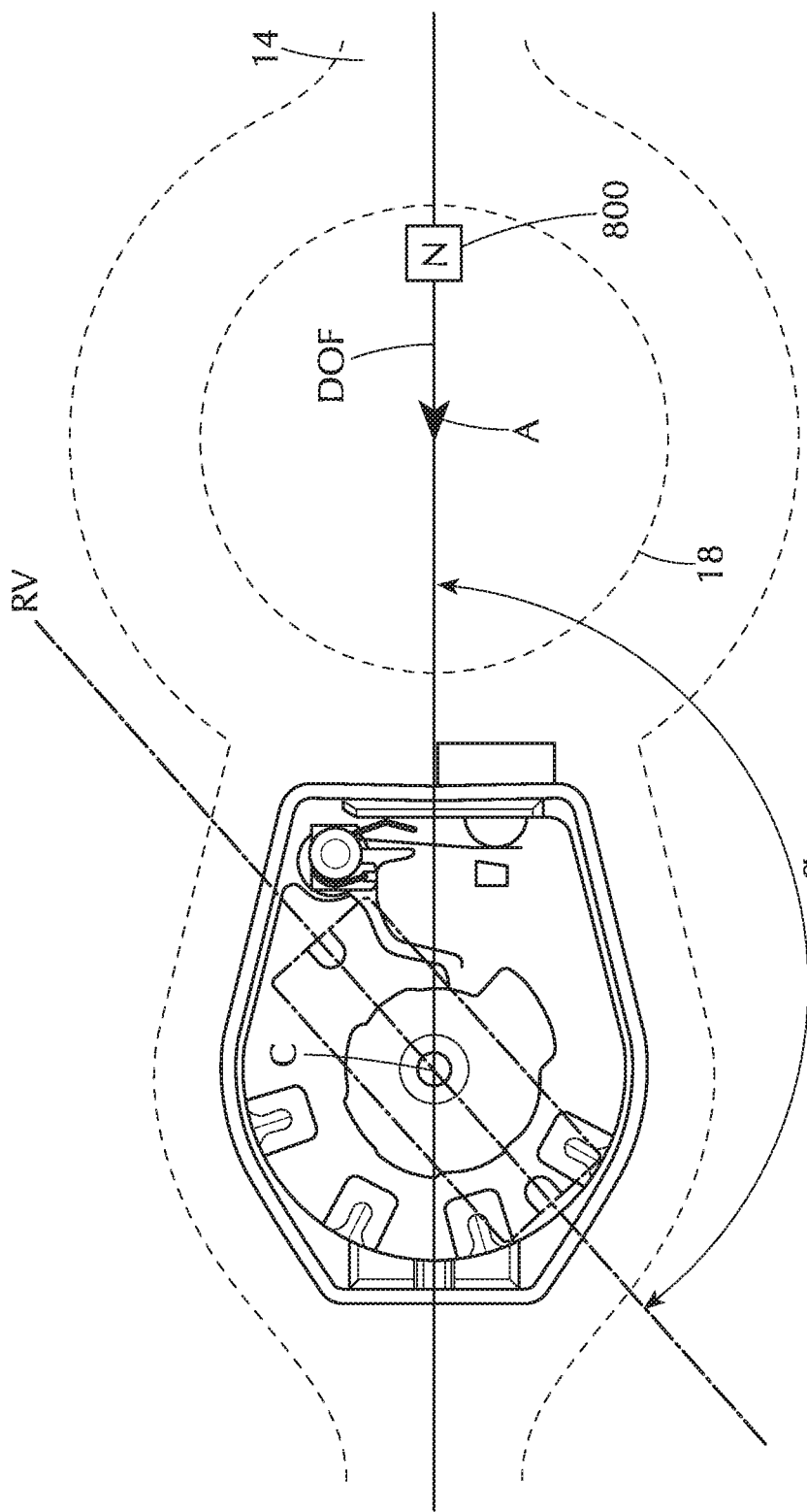
FIG. 6I is a partial cross-sectional view of the adjustable valve unit of FIG. 4 at an exemplary first pressure setting illustrating the arrow marking on the programmable valve device denoting a direction of fluid flow therethrough and a fixed reference magnet.
Figure 6J:
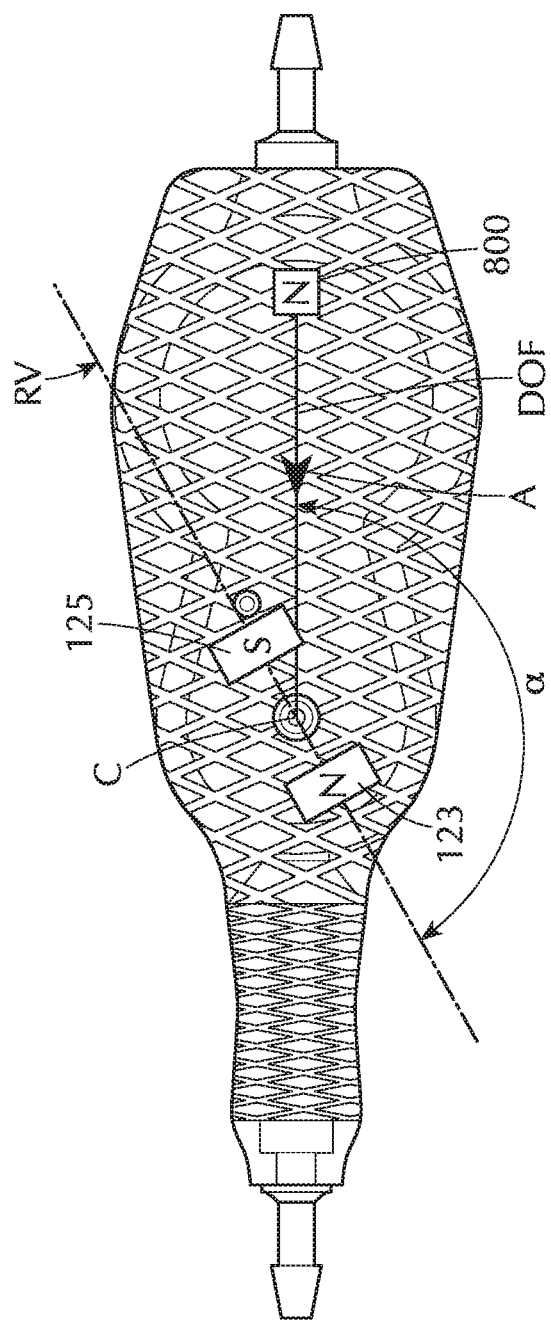
FIG. 6J is a top view of the programmable valve device of FIG. 1 wherein the adjustable valve unit is at the same first pressure setting illustrated in FIG. 6I and also showing the direction of flow arrow marking and positioning of the fixed reference magnet.

As discussed above, the programmable valve 10 includes a fixed reference magnet 800, in addition to the primary magnetic elements 123, 125 disposed in the housing 124 of the rotor 120 of the adjustable valve unit, as illustrated in FIG. 6I. Referring to FIG. 6J, by way of illustrated example, the fixed reference magnet 800 is located in the valve between the proximal connector 14 and the sampling/pumping chamber 18 within the direction of flow of the valve. However, the location of the fixed reference magnet 800 in the valve may be altered, as desired. In addition, instead of being disposed in the implantable valve itself, the fixed reference magnet 800 could be on a card that is placed externally overtop the valve/patient tissue to aid an electronic tool. Preferably, fixed reference magnet 800 has a different magnetic strength (nominal $2.7 \times 10^{\wedge-9}$ Weber Meter) from the primary magnetic elements (nominal $3.2 \times 10^{\wedge-9}$ Weber Meter) 123, 125 and a different nominal distance between magnets (i.e., distance between reference magnet 800 and primary magnet 123 compared to distance between primary magnets 123 and 125) for proper identification by the sensor array. Nominal distance between primary magnetic elements 123, 125 is approximately 5.48 mm measured from bottom inner corner to bottom inner corner. Fixed reference magnet 800 nominal distance is approximately 17.5 mm from the rotating construct axle to leading edge of reference magnet 800. Fixed reference magnet 800 is aligned with an arrow indicia or marking "A" on the programmable valve 10 itself denoting the direction of flow of fluid therethrough and a center point "C" midway between the magnetic elements 123, 125. A line passing through these three points (referred to as a direction of flow line) is the basis for determining the orientation of the programmable shunt valve 10 using an integrated locator/indicator tool 1405 from the exemplary tool set 1400 in a case, as illustrated in FIG. 14. It is noted that the locator and indicator tools described herein and illustrated in the accompanying drawings have been integrated into a single device for simplicity of operation, but could be two distinct devices. It is, however, contemplated and within the intended scope of the present invention for some, none, or all of the tools of the toolset to be integrated. Also included in the toolset is an adjustment tool 1415, a screwdriver 1410 and spare batteries 1408.

Figure 14A:
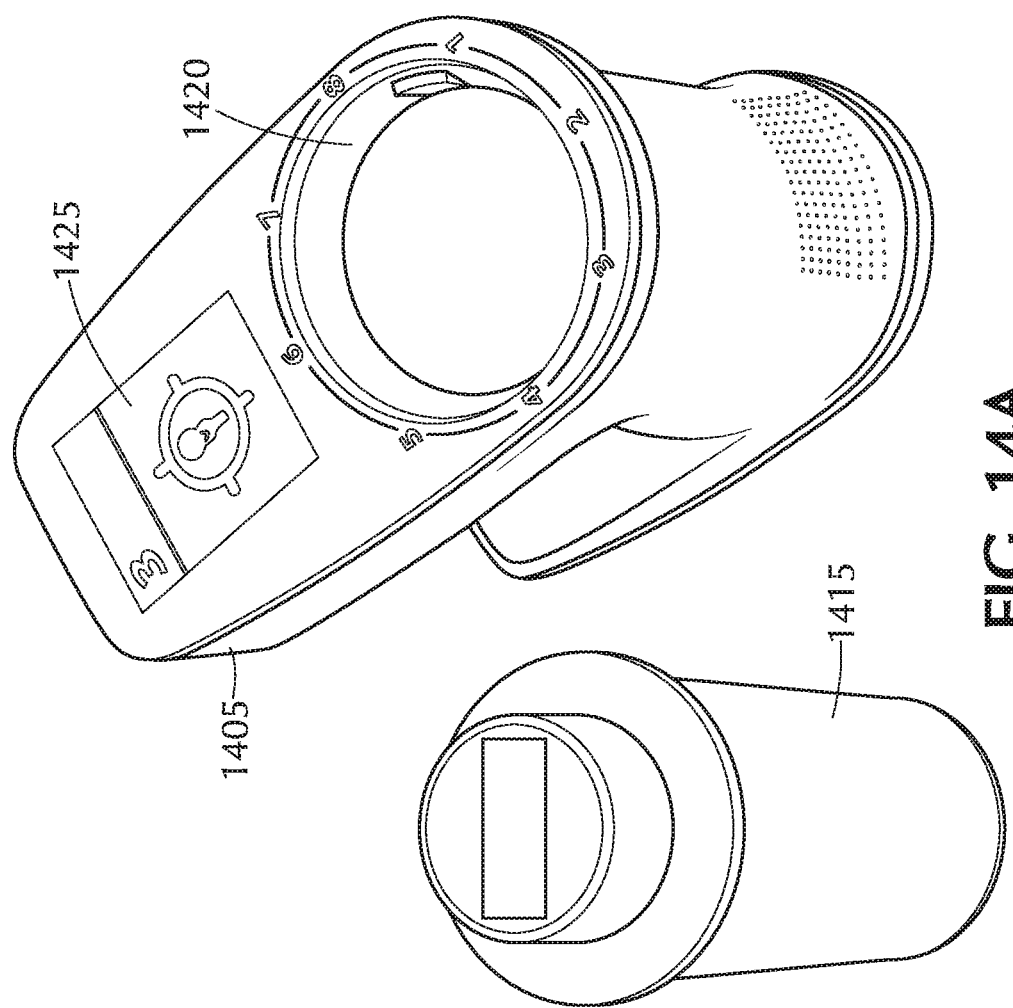
FIG. 14A is a top perspective view of the integrated locator/indicator tool and adjustment tool of FIG. 14, prior to the adjustment tool being inserted into the integrated locator/indicator tool.
Figure 14B:
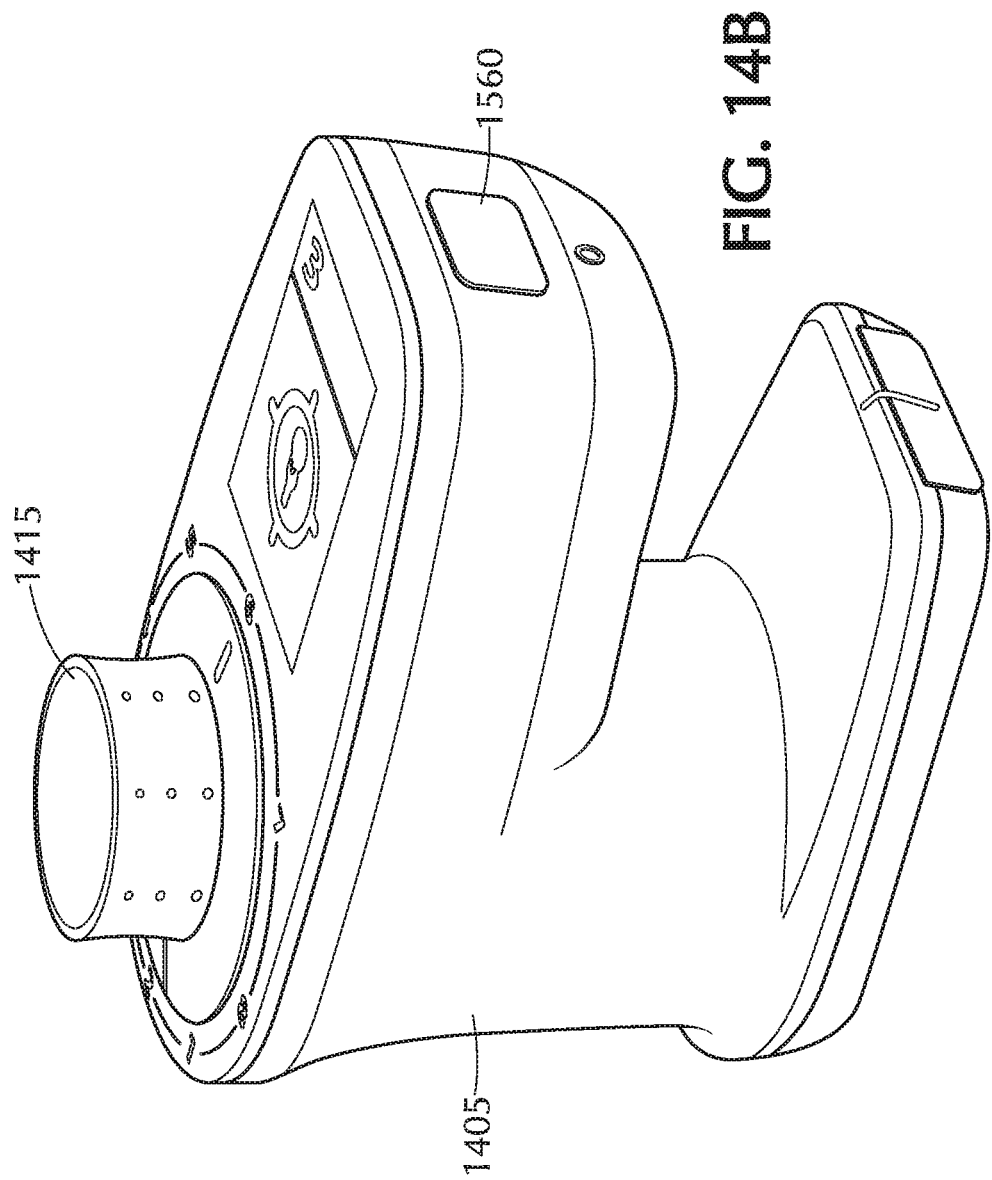
FIG. 14B is a top perspective view of the integrated locator/indicator tool and adjustment tool of FIG. 14, with the adjustment tool inserted into a complementary cavity in the integrated locator/indicator tool.

A top perspective view of the integrated locator/indicator tool 1405 and adjustment tool 1415 of FIG. 14, prior to the adjustment tool 1415 being inserted into a cavity 1420 of the integrated locator/indicator tool 1405, is shown in FIG. 14A. While FIG. 14B shows the adjustment tool 1415 following insertion into the cavity 1420.

Figure 15:
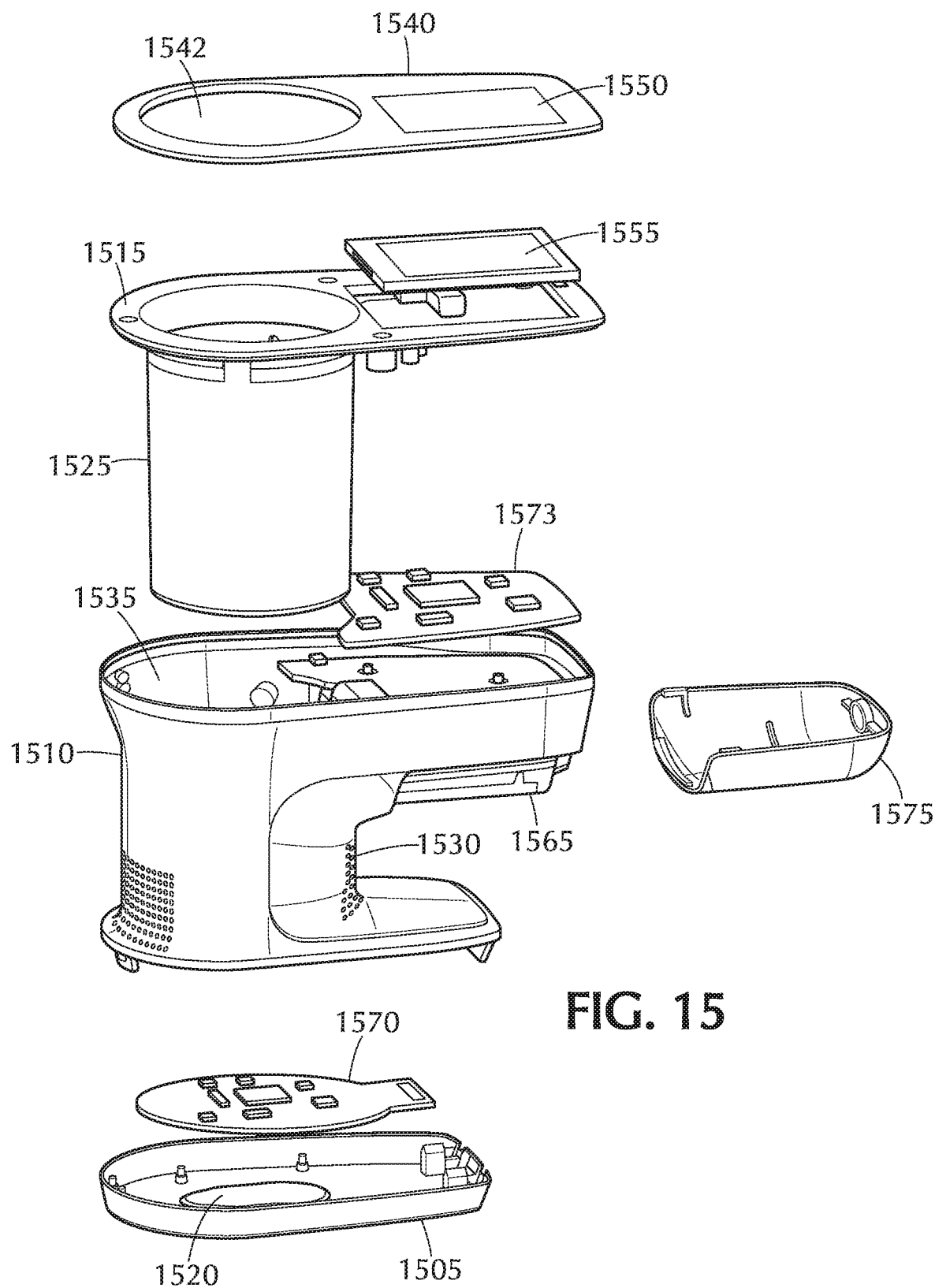
FIG. 15 is an exploded perspective view of the integrated locator/indicator tool of FIG. 14.

FIG. 15 is an exploded perspective view of the integrated locator/indicator tool 1405 of FIG. 14 which includes a housing. In the illustrated example, the housing comprises a bottom housing section 1505, a middle housing section 1510 and a top housing section 1515, each separate from one another. A cylindrical shaped section 1530 of the middle housing section 1510 defines a passageway or channel 1535 extending longitudinally therethrough. Top housing 1515 has a chimney 1525 complementary in size and shape to be received within the passageway or channel 1535 of the cylindrical shaped section 1530 of the middle housing section 1510. Chimney 1525 is closed at one end and open at an opposite end. The open end of the chimney 1525 receiving therein the adjustment tool 1415, as described in detail below. An exterior surface of the bottom housing 1505 has a recess 1520 defined therein that is complementary in shape and size to the outer contour of the programmable implantable bodily fluid drainage valve. In use, the integrated location/indication tool 1405 is positioned with the exterior surface of the bottom housing 1505 against the skin of the patient and the implantable bodily fluid drainage valve seated within the recess 1520. A top covering or layer 1540 may be mounted to the top of the assembled housing. Such covering or layer 1540 has a complementary size and shape opening 1542 to that of the chimney 1525. Disposed about the perimeter of the opening 1542 are a series of markings or indicia representing the different valve settings in predetermined increments (e.g., 1, 2, 3, 6, 7, 8). A second opening 1550 in the top covering or layer 1540 permits viewing therethrough of a display 1555, such as a Liquid Crystal Display (LCD). The integrated locator/indicator tool 1405 is powered by one or more batteries and turned ON/OFF by a button 1560. The batteries are housed within a battery enclosure assembly 1565 that includes a tray with conventional electronic contact terminals between which the batteries are inserted. Access to the battery enclosure assembly 1565 for insertion/removal of the batteries therefrom is via a removeable battery door assembly 1575. A two-dimensional array of 3-axis magneto-resistive sensors 1570 printed on a circuit board independently detects the magnetic field pattern produced by each of the magnetic elements 123, 125 disposed in the housing 124 of the rotor 120 and the fixed reference magnet 800. It is within the intended scope of the present invention to substitute other types of sensor arrays capable of detecting magnetic fields, such as Hall sensors, for the 3-axis magneto-resistive sensors 1570. Another printed circuit board 1573 includes a processor/controller, memory device and other electronic circuitry.

Figure 16:
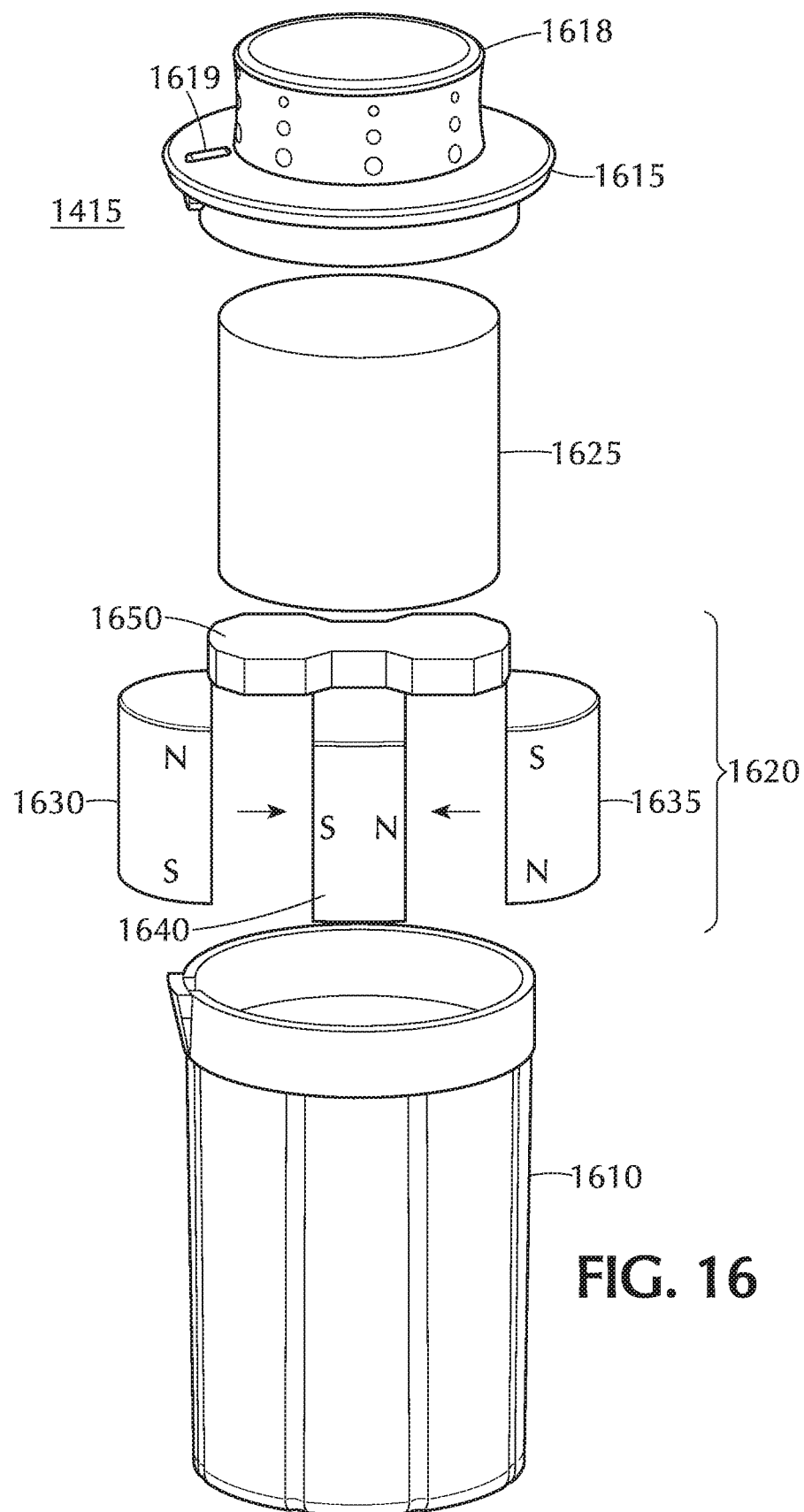
FIG. 16 is an exploded perspective view of the adjustment tool of FIG. 14.
Figure 16A:
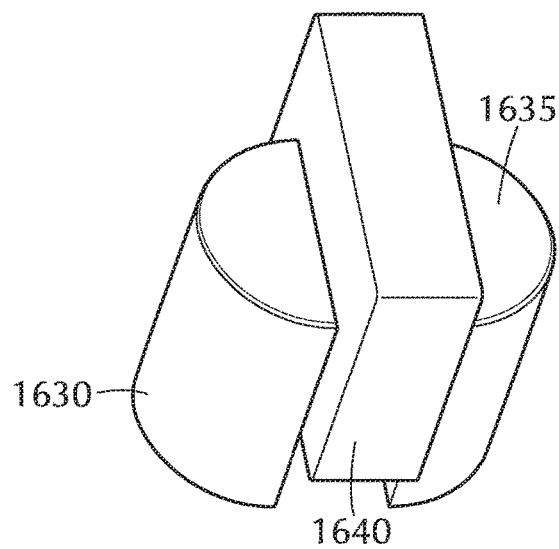
FIG. 16A is a perspective view of the placement of the half round magnets on either side of the magnet shield comprising part of the magnet assembly of FIG. 16.
Figure 16B:
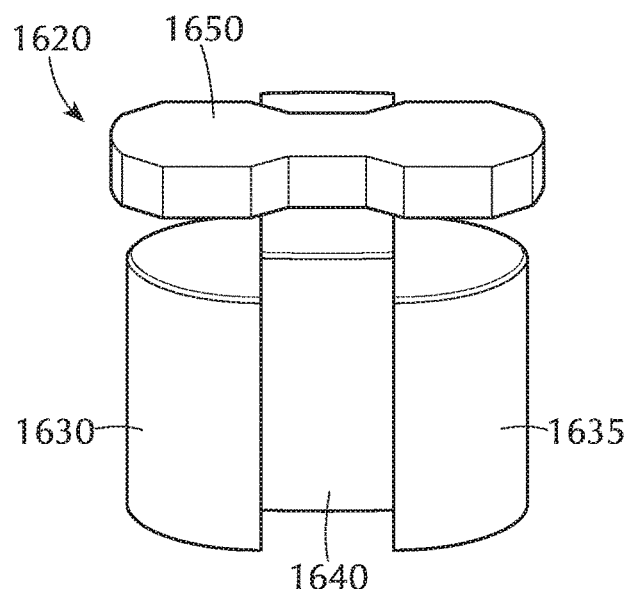
FIG. 16B is a perspective view of the assembled magnet assembly of FIG. 16.
Figure 16C:
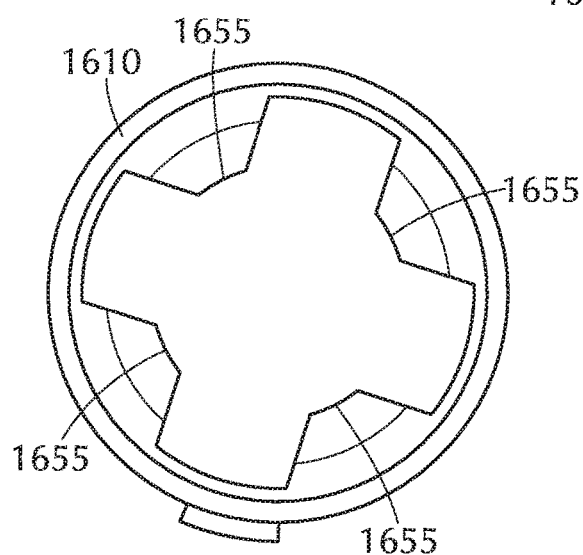
FIG. 16C is a top view of the assembled bottom and middle housing sections of the adjustment tool of FIG. 16 showing the internal vertical ribs.
Figure 16D:
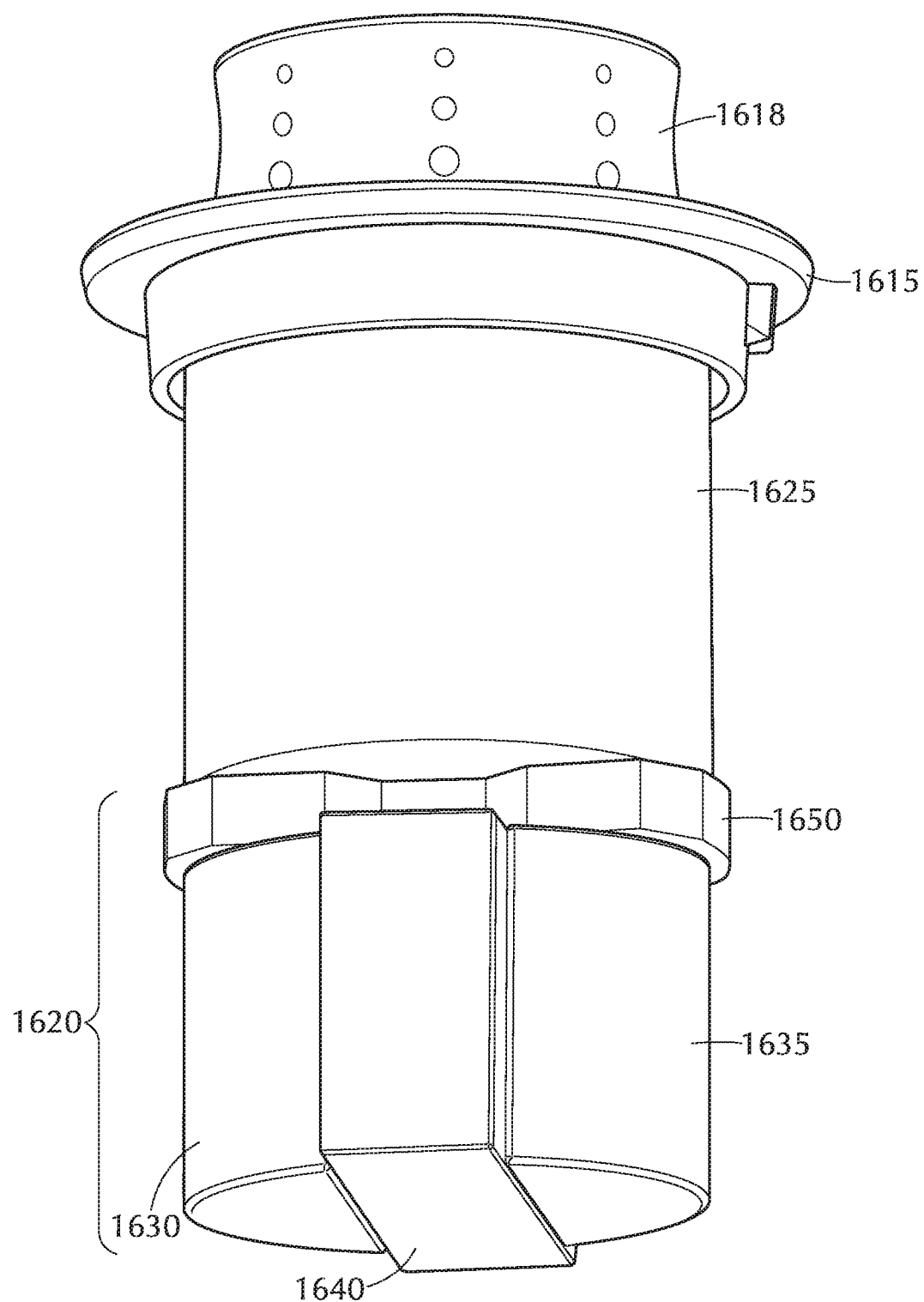
FIG. 16D is a perspective view of the assembled adjustment tool of FIG. 14 without the outer housing section to illustrate the magnet assembly.

FIG. 16 is an exploded perspective view of the adjustment tool 1415 of FIG. 14. In the illustrated example, housing 1600 comprises an outer housing section 1610 and a top housing section 1615, each separate from one another. A magnet assembly 1620 is disposed in the outer housing section 1610. In particular, the magnet assembly 1620 in FIG. 16A is a Halbach array comprising two half round magnets 1630, 1635 connected by a yoke 1650 and separated by a shield magnet 1640 that redirects the magnetic field allowing deeper penetration. The strength of the half round magnets 1630, 1635 selected for use in the adjustment tool 1415 depends on one or more factors, such as distance from the valve and the design of the sensor array. In the magnet assembly 1620, the two half round magnets 1630, 1635 are rotated until their flat side lays flush against the shield magnet 1640, as depicted in FIGS. 16, 16A, 16B & 16D. The orientation of the magnets 1640, 1630, 1635 should preferably with the magnet north side of the shield magnet 1640 in contact with the half round magnet 1630, 1635 with a magnetic north pointed toward the bottom of the outer housing section 1610. One of the two half round magnets 1630, 1635 faces the tantalum reference ball 129 (FIG. 13). The shield magnet 1640 is partially repelled by the half round magnets 130, 1635 and thus is held down by a yoke 1650 mounted on top of the shield magnet 1640 that, when assembled, is also in contact with the two half round magnets 1630, 1635. It is these components of the magnet assembly 1620 that when assembled together are inserted into the outer housing section 1610 so that the two half round magnets 1630, 1635 are received in respective recesses defined in an interior surface of the outer housing section 1610 with the half round magnet facing the tantalum ball 129 facing towards the '1 to 8 stop'. As is visible in the top view in FIG. 16C, the outer housing section 1610 includes a plurality of vertical ribs 1655 with which the half round magnets 1630, 1635 connect. A cylindrical shaped spacer 1625 is positioned above the yoke 1650 (FIG. 16D). The top housing section 1615 with a marking indicator is secured to the outer housing section 1610 forming the assembled adjustment tool 1415.

The magnetic field pattern produced by each of the magnetic elements 123, 125 disposed in the housing 124 of the rotor 120 and the fixed reference magnet 800 is detected by the two-dimensional array of 3-axis magneto-resistive sensors 1570 of the integrated locator/indicator tool 1405. Once these three magnets are detected, the center point "C" midway between the two detected magnetic elements 123, 125 is located (FIG. 6J). A direction of flow line "DOF" (i.e., reference line) is identified as passing through the detected fixed reference magnet 800, the arrow indicia or marking "A" denoting the direction of flow on the implantable valve, and the center point "C" midway between the two detected magnetic elements 123, 125. A rotating vector "RV" is defined connecting the two detected magnetic elements 123, 125. Thereafter, a rotating construct angle α is measured between the direction of flow line "DOF" and the rotating vector "RV". Specifically, the rotating construct angle α is measured starting from the direction of flow line "DOF" (as a staring reference line) traveling in a counter-clockwise direction until intersecting with the rotating vector "RV".

Once the rotating construct angle α has been ascertained based on the detected three magnets in the adjustable valve unit the value is compared to stored predetermined mechanical angular spacing values for each of the setting pockets for that particular implantable valve, as described in further detail below. If a match exists between the measured rotating construct angle α and the predetermined mechanical angular spacing of any of the setting pockets, then the magnetic field resistance mechanism is deemed properly locked or engaged. Otherwise, if the measure rotating construct angle α does not match the predetermined mechanical angular spacing of any of the setting pockets, then the magnetic resistance mechanism is found not to be properly locked or engaged. A visual indictor (e.g. text and/or icon) may be generated on display 1555 of the integrated locator/indicator tool 1405 confirming when the magnetic field resistance mechanism is properly engaged and/or found not to be properly engaged. In addition to such visual display indicator, a tactile indicator may be provided. If the magnetic field resistance mechanism is not properly engaged, instructions and steps to be taken to reprogram the valve setting using the adjustment tool 1415 and thereafter once again confirm whether or not the magnetic field resistance mechanism is properly engaged may be provided on display 1550 of the integrated locator/indicator tool 1405.

Preferably, each time a valve setting is programmed using the adjustment tool 1415 the integrated locator/indicator tool 1405 in accordance with the present invention is thereafter used to confirm whether the magnetic field resistance mechanism is properly locked or engaged. Alternatively, the present inventive integrated locator/adjustor tool 1405 may be employed to verify proper engagement of the magnetic field resistance mechanism prior to intentional exposure to a foreign magnet, e.g., before an (MRI) procedure.

As previously mentioned, based on the particular design of the valve, a predetermined mechanical angular spacing relative to the direction of flow of the shunt valve as (identified by the arrow marking "A") is associated with each of the setting pockets 171, 171', 171", 171'. Each setting pocket 171, 171', 171", 171' is bound on at least one side by a lock stop. Depending on the valve configuration, in some designs such as the Strata® programmable valve, each setting pocket is bounded on either side by adjacent lock stops. That is, each lock stop has a clockwise leading edge and a counter-clockwise leading edge. Therefore, each setting pocket is bounded on one side by a counter-clockwise leading edge of a first lock stop and on the other side by a clockwise leading edge of a second lock stop adjacent to the first lock stop. Whether the setting pocket is bound by one or two lock stops, in either case, the mechanical angular spacing or width in degrees of each of the setting pockets for a particular programmable valve may be dynamically adjusted based on skin depth since it has been found that the fixed reference magnet may influence identification of the setting pockets that vary slightly as you get farther away from the valve. Distance between rotating construct magnets may be used to determine depth. Thus, the mechanical angular spacing or width is controlled by the design of the valve. The sensor array does not identify the pockets, but the magnetics are not as simple as just measuring the fields. Characterization has shown that the magnetic fields change based on distance away from the sensor array of the integrated locator/indicator tool. Therefore, the actual boundaries of the setting pockets change based on the distance from sensor array. This has been confirmed by testing of multiple valves at extremes on setting pocket location and distance from locator/indicator tool. An algorithm determines distance and calculates where the boundary should be based on pre-measured valves. The predetermined mechanical angular spacing for each setting pocket is represented by two mechanical angular boundary values defining either side of the setting pocket. A first mechanical angular boundary value representing the mechanical angle of the leading edge of each lock stop traveling in a counter-clockwise direction starting from the direction of flow as a reference, while the second mechanical angular boundary measurement represents the mechanical angle when the constant angular width of the setting pocket is added to the first mechanical angular boundary measurement in a clockwise direction. It is the first and second mechanical angular boundary values that represent the predetermined mechanical angular spacing for that particular setting pocket. The first and second mechanical angular boundary values for each setting pocket of a particular programmable valve are ascertained in advance and stored in memory, for example, in the locator/indicator tool.

FIGS. 6A-6H are exemplary illustration of 8 different pressure settings and their associated setting pockets for the CODMAN CERTAS® Plus Programmable Valve. In which some of the setting pockets are bound by adjacent lock stops (e.g., 170-172; 172-174; 174-176), while others are only bound by a single lock stop (e.g., 176). The mechanical angular spacing for each setting pocket for the CODMAN CERTAS® Plus Programmable Valve configuration is provided below in Table 1.

TABLE 1

| Pressure Settings | Setting Pocket (defined by one or more lock stops) | Mechanical Angular Spacing Clockwise from direction of flow "A" |
|---|---|---|
| $1^{st}$ & $5^{th}$ | Between lock stops 170, 172 | −29° to −53° |
| $2^{nd}$ & $6^{th}$ | Between lock stops 172, 174 | −3° to 20° |
| $3^{rd}$ & $7^{th}$ | Between lock stops 174, 176 | 37° to 65° |
| $4^{th}$ & $8^{th}$ | Between lock stops 176, 170 | 82° to 109° |

Figure 17A:
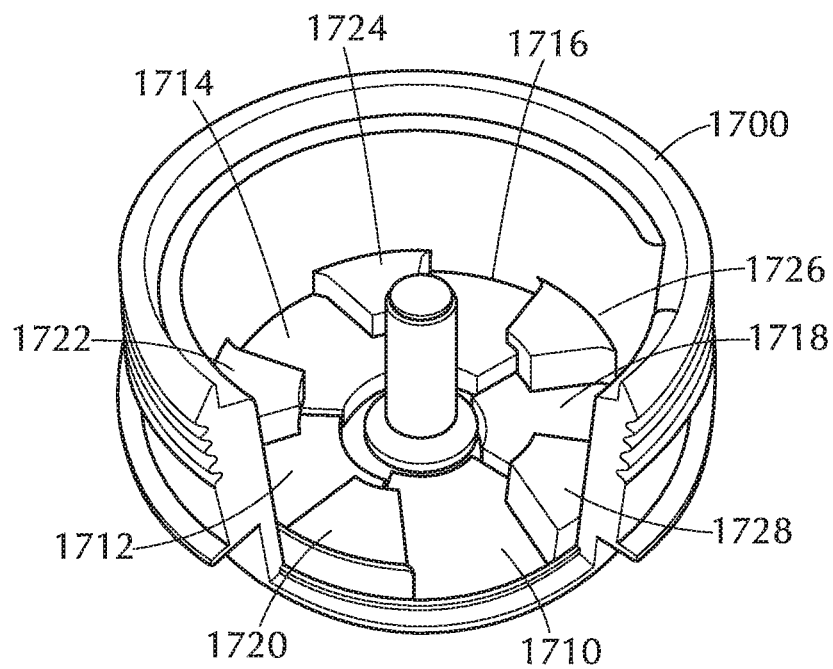
FIG. 17A is a perspective view of an alternative configuration of the lower casing of the adjustable valve unit.
Figure 17B:
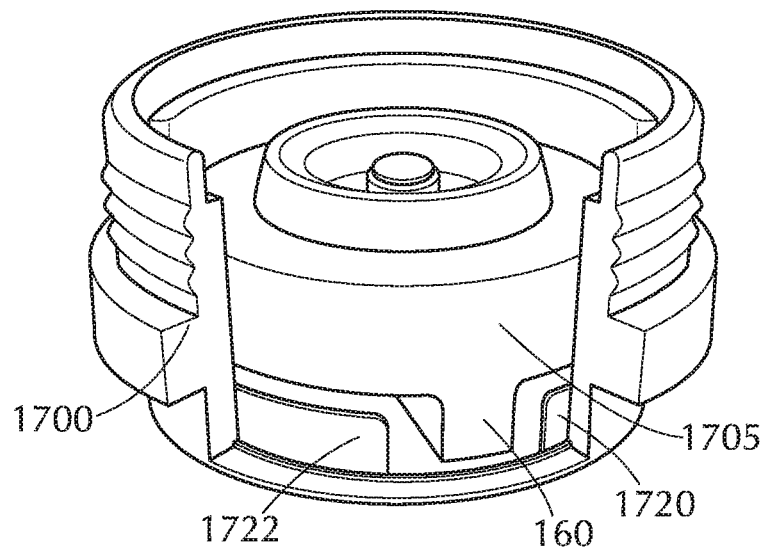
FIG. 17B is a perspective view of the alternative configuration of the lower casing of FIG. 17A with the rotating construct nested therein.

Referring to FIGS. 17A & 17B, the lower casing 1700 and rotating construct 1705 of the Strata® Programmable Valve has a different configuration than that of the CODMAN CERTAS® Plus Programmable Valve. Specifically, the five setting pockets 1710, 1712, 1714, 1716, 1718 are arranged in the lower casing 1700 in a 360-degree circular configuration, each setting pocket interposed between adjacent lock stops 1720, 1722, 1724, 1726, 1728. That is, each of the five setting pockets 1710, 1712, 1714, 1716, 1718 is defined on the one side by a clockwise leading edge of a first lock stop and on the other side by a counter-clockwise leading edge of a second lock stop adjacent to the first lock stop. Therefore, each of the five setting pockets has a constant angular width or mechanical angular spacing.

The present inventive safety feature is also applicable to other configurations wherein the magnetic field resistance mechanism, when properly engaged or locked, has one or more structural components seated within corresponding cavities/pockets/recess. Rather than one or more downward projecting teeth being received in respective setting pockets defined by one or more lock stops (as described above), one alternative design is set forth in U.S. Pat. No. 5,643,194 (herein incorporated by reference in its entirety) as illustrated in FIGS. 18A & 18B in which cylindrical shaped mating lead in elements or components are received within respective complementary shaped cavities, notches, openings or pockets.

Figure 18A:
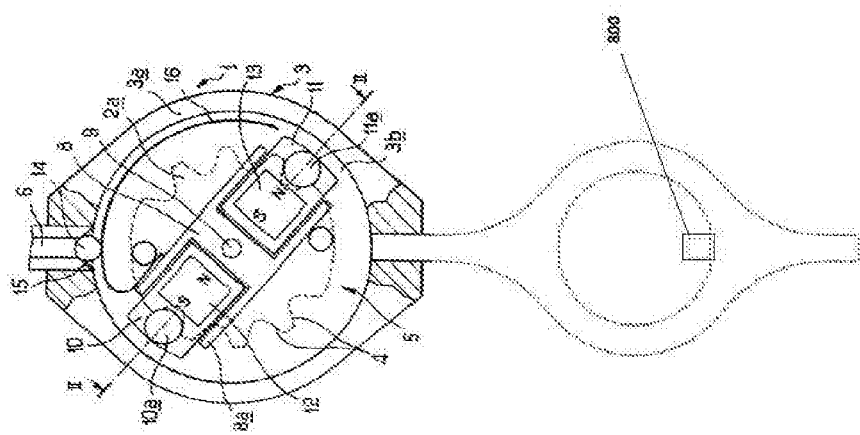
FIG. 18A is an alternative configuration of a prior art programmable valve.
Figure 18B:
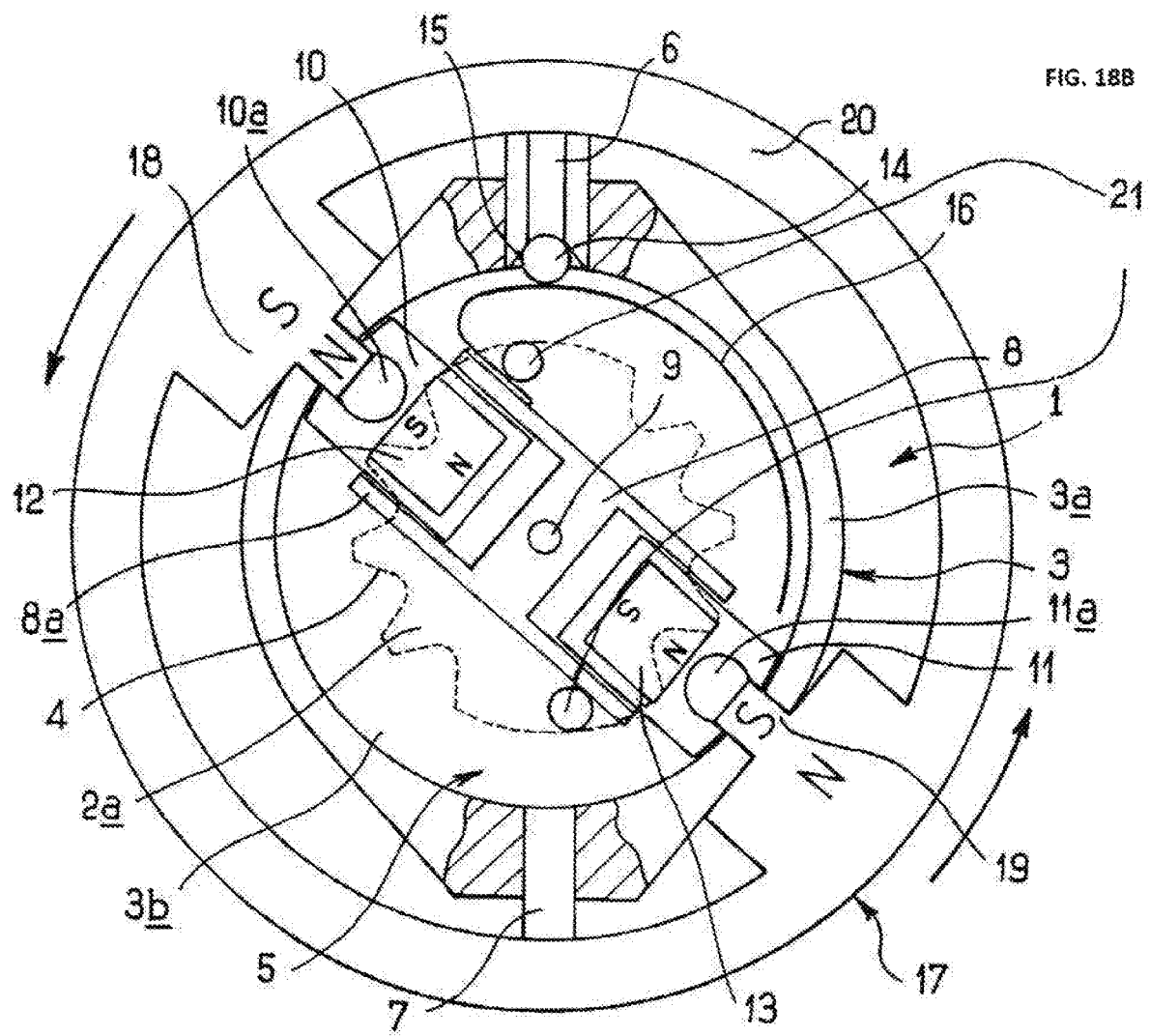
FIG. 18B is a prior art setting device for use with the programmable valve of FIG. 18A.

The plan view in FIG. 18A depicts a valve body 1, without its upper cover, and a casing 3. Cavities 4, represented in broken line in FIGS. 18A & 18B, are formed at the periphery of a substantially cylindrical central part 2a. The valve body 1 includes a cylindrical and flat internal chamber 5 formed between the lower wall 3b, a lateral wall 3a of the casing 3 and upper cover 2. An inlet pipe 6 and a drain pipe 7 are formed in the lateral wall 3a of the casing 3, the inner ends of the said pipes 6 and 7 being arranged diametrically in the chamber 5. The inlet pipe 6 and the drain pipe 7 are connected respectively to a catheter for supplying fluid and to another catheter for draining fluid away.

A rotating construct or rotor 8 comprising an H-shaped bar is rotatably mounted in the chamber 5 about central axis 9. Stop elements 21 projecting from a lower wall 3b of the casing 3 are provided to limit the rotational displacement of the rotor 8. The rotor 8 includes lateral branches 8a which serve as guide means, on either side of the central axis 9, for moving parts 10 and 11 each housing a micro-magnet 12 and 13, respectively with opposing faces of the micro-magnets 12, 13 being of opposite polarity (N and S). Moving parts 10 and 11 are displaced linearly inside the rotor 8 in a substantially radial direction thereof to actuate the locking mechanism. In particular, the locking mechanism comprises a circular succession of open mating pockets, notches or cavities 4 defined radially inward along an outer perimeter of the substantially cylindrical central part 2a for receiving complementary shaped mating lead in elements 10a and 11a (for example, cylindrical lugs) projecting respectively from the moving parts 10 and 11. Between adjacent open notches or cavities 4 are portions of the substantially cylindrical central part 21 hereinafter referred to as dividing posts.

The valve body 1 includes a non-return valve consisting of a ball 14 and of a cone-shaped seat 15 arranged at the inner end of the inlet pipe 6. A semi-circular leaf spring 16 is fixed to one lateral branch 8a of the rotor 8, parallel to the lateral wall 3a of the chamber 5 and compresses the ball 14 into its seat 15 to regulate, and if appropriate block, the passage of fluid into the chamber 5 via the inlet pipe 6. As in the valve design in FIG. 1, the alternative valve design in FIG. 18A may also include a fixed reference magnet 800.

FIG. 18B represents a prior art external setting device 17 arranged on the valve body 1 of FIG. 18A. The external setting device 17 includes two magnets 18 and 19, for example made of samarium-cobalt, the opposing faces of which are of opposite polarities to (N and S) and of greater magnetic mass than the moving micro-magnets 12 and 13 associated with the valve body 1. The magnets 18 and 19 are mounted on a common annular support 20, for example made of soft iron, diametrically opposed and spaced apart by a distance substantially equal to or greater than the distance separating the outer poles of the two moving micro-magnets 12 and 13 when the lugs 10a and 11a are engaged in the notches or cavities 4.

The operation of the external setting device 17 in FIG. 18B will now be described. FIG. 18A represents the valve body 1 in its locked position, that is, with the cylindrical lugs 10a, 11a both engaged in respective notches or cavities 4 and locked in place therein as a result of magnetic attraction brought about by the opposite polarities of the micro-magnets 12, 13.

FIG. 18B represents the valve body 1 in its unlocked position, wherein the cylindrical lugs 10a, 11a are both disengaged from the notches or cavities 4. In order to unlock the valve (disengage or unseat the cylindrical lugs 10a, 11a from the respective notches or cavities 4), the external setting device 17 illustrated in FIG. 18B is aligned vertically with the valve body 1 so that the magnets 18, 19, the opposing faces of which have opposite polarities (N and S), are positioned symmetrically with respect to the central axis 9 of the chamber 5 and on either side of the micro-magnets 12, 13. Of course, the strength of the magnets 18, 19 has to be greater than that of the micro-magnets 12, 13 to overcome the attraction force which exists between the micro-magnets 12, 13.

Bearing in mind the difference in magnetic mass which exists between the magnets 18, 19 of the external setting device 17 and the micro-magnets 12, 13 of the valve, the simple fact of bringing the N and S poles of the setting device close to the opposite S and N poles of the micromagnets, subjects the two outer poles of the micro-magnets 12, 13 to a peripheral attraction which is greater than the central mutual attraction between the two inner poles. This results in the two micro-magnets 12, 13 together with their moving parts 10, 11 separating symmetrically and simultaneously towards the periphery of the chamber 5, which unlocks or disengages the rotor 8 and renders it free to rotate. With the rotor 8 thus unlocked or disengaged, it is possible to alter its position and consequently to alter the operating pressure and throughput of the valve, by pivoting the setting device 17 about the central axis of the chamber of the valve, which simultaneously drives the rotor along. In order to lock the rotor 8 in a new desired position, the setting device 17 is withdrawn, moving it away vertically with respect to the plane of the valve. Since the two micro-magnets 12, 13 are no longer subjected to external peripheral attraction with the magnets 18, 19, the micro-magnets 12, 13 approach each other once again under the effect of their mutual attraction, thus seating (i.e., locking) the lugs 10a, 11a into the respective notches or cavities 4.

This type of valve with moving micro-magnets provides magnetic field resistance against a change in valve setting in the presence of a strong external foreign magnetic or electromagnetic field, because the two moving micro-magnets 12, 13 cannot simultaneously disengage from their cavity in the presence of a unidirectional magnetic field. Insofar as the two moving micro-magnets 12 and 13 are arranged on either side of the central axis of the valve, when one of the micro-magnets is attracted towards the periphery of the chamber, the other is repelled into a locking cavity. An external setting device like the one illustrated in FIG. 18B is required to unlock or disengage the valve, that is to say in order to separate the micro-magnets 12, 13 symmetrically.

However, the valve shown in FIGS. 18A & 18B and described above is not susceptible to change in valve setting when exposed to foreign magnets only if the cylindrical lugs 10a, 11a are properly seated, engaged or locked in the respective notches or cavities 4. Similar to the discussion above with respect to the CODMAN CERTAS® Plus Programmable Valve once again there is the possibility that when unlocked the lugs 10a, 11a will come to rest against a region of the outer perimeter of the substantially cylindrical central part 2a herein after referred to as a dividing post (region along the outer perimeter of the substantially cylindrical central part 2a between adjacent notches or cavities 4) rather than properly seated or engaged in a respective notch or cavity 4.

In accordance with the present invention, there are two different ways to determine whether the valve in FIG. 18B is properly locked in place (i.e., whether cylindrical lugs 10a, 11a are properly engaged or seated in a respective notch or cavity 4). If the valve in FIG. 18B includes a fixed reference magnet 800, one method by which proper engagement may be verified is based on the detected angular position of the micro-magnet 12 (following the methodology described in detail above using the integrated locator/indicator tool 1405). Once the angular position of the micro-magnet 12 has been determined it is compared to the predetermined angular spacing of the respective notches or cavities 4. If the detected angular position of the micro-magnet 12 matches the predetermined angular spacing of one of the respective notches or cavities 4 then the valve is deemed to be properly locked (i.e., the lugs 10a, 11a are properly engaged or seated in respective notches or cavities 4). Otherwise, if the detected angular position of the micro-magnet 12 does not match the predetermined angular spacing of any of the respective notches or cavities 4 then the valve is not properly locked (i.e., the lugs 10a, 11a are resting on the dividing posts). In such latter case, the user is instructed to adjust the valve using the external setting device 17 once again and thereafter confirm whether the valve is properly engaged, seated or locked.

An alternative method for confirming whether the valve of FIG. 18B is locked or properly engaged is based on the measured distance between the center of the two micro-magnets 12, 13. As discussed in detail above, with the external setting device 17 withdrawn from the valve, the micro-magnets 12, 13 attract one another holding them in place. If the micro-magnets 12, 13 are properly seated, engaged or locked in respective notches or cavities 4, then the distance separation between the center of the micro-magnets 12, 13 will be a predetermined proper locking value. Otherwise, if the micro-magnets 12, 13 are instead resting along the outer perimeter of the substantially cylindrical central part 2a between two adjacent notches or cavities 4 (i.e., on a dividing post) then the centers of the respective micro-magnets 12, 13 will a greater distance separation from one another then the predetermined locking value. Thus, this alternative method may also use the same integrated locator/indicator tool 1405 to detect the centers of the respective micro-magnets 12,13 on the rotating construct and measure the distance therebetween, a comparison is thereafter made with the predetermined locking value. Of course, the algorithm for the integrated locator/indictor tool 1405 would have to be modified accordingly for this alternative method. If the measured distance is equal to the predetermined locking value indicating proper locking then the valve is deemed to be properly engaged or locked (i.e., the lugs 10a, 11a, are properly seated in the respective notches or cavities 4), whereas if the measured distance is greater than the predetermined locking value the valve is deemed to be improperly engaged or not locked (i.e., the lugs 10a, 11a are resting on dividing posts). As with the other embodiments, the user is instructed to reprogram the valve to the desired setting and once again confirm that the valve is properly locked or engaged.

The present inventive improved toolset employing a sensor array for use with a programmable valve provides the additional safety feature of verifying whether the magnetic field resistance functionality of the valve is properly engaged. This additional safety feature may be invoked every time the valve is programmed to a new setting or prior to exposure to a foreign magnet, for example, before an MRI procedure. The inventive toolset with this additional safety feature is suitable for use with any type of programmable valve which when locked in place has a structural component seated or engaged in a corresponding notch, recess, cavity, pocket or other complementary shaped region.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for verifying whether a magnetic field resistance mechanism is properly engaged in an implantable programmable bodily fluid drainage system comprising an implantable bodily fluid drainage valve having an adjustable valve unit including a rotating construct and a pair of primary magnetic elements for programming the adjustable valve unit to a desired valve setting, the method comprising the steps of:

determining using a toolset whether the magnetic field resistance mechanism is properly engaged;

generating an alert whether the magnetic field resistance mechanism is at least one of properly engaged or not properly engaged.

2. The method according to claim 1, wherein the step of determining whether the magnetic field resistance mechanism is properly engaged is based on: (i) a measured angular position of a detected one of the pair of primary magnetic elements relative to a direction of flow of fluid through the implantable bodily fluid drainage valve; and/or (ii) a measured distance separation between respective centers of the detected pair of primary magnetic elements.

3. The method according to claim 2, wherein the determining step determines whether the magnetic field resistance mechanism is properly engaged based on the measured angular position of the detected one of the pair of primary magnetic elements relative to the direction of flow of fluid through the implantable bodily fluid drainage valve.

4. The method according to claim 3, wherein the implantable bodily fluid drainage valve includes a fixed reference magnet aligned with a marking on the implantable bodily fluid drainage valve denoting the direction of flow of fluid therethrough and a center point midway between the detected pair of primary magnetic elements; and the housing of the rotating construct comprises an upper casing having a plurality of downward projecting teeth in which the pair of primary magnetic elements are respectively located and a lower casing including a plurality of corresponding setting pockets for receiving the downward projecting teeth; wherein each of the setting pockets is bound on at least one side by a lock stop projecting upwardly from the lower casing towards the upper casing,
  wherein the determining step comprises:
    detecting using a sensor array in the toolset a magnetic field pattern produced by each of: (i) the fixed reference magnet; and (ii) the pair of primary magnetic elements;
    locating the center point midway between the detected pair of primary magnetic elements;
    defining a direction of flow line as a reference line intersecting with: (i) the marking denoting the direction of flow of fluid through the implantable bodily fluid drainage valve; (ii) the located center point midway between the detected pair of primary magnetic elements; and (iii) the detected fixed reference magnet;
    defining a rotating construct vector connecting the centers of the detected pair of primary magnetic elements;
  measuring a rotating construct angle starting from the defined direction of flow line traveling in a counter-clockwise or clockwise direction until intersecting the rotating construct vector;
    comparing the measured rotating construct angle to a predetermined mechanical angular spacing for each of the setting pockets as stored in a memory device; wherein if the measured rotating construct angle matches the predetermined mechanical angular spacing for any of the setting pockets then the magnetic field resistance mechanism is deemed properly engaged; otherwise, if the measured rotating construct angle does not match the predetermined mechanical angular spacing for any of the setting pockets then the magnetic field resistance mechanism is deemed not to be properly engaged.

5. The method according to claim 4, wherein the fixed reference magnet is disposed between a proximal connector and a pumping chamber of the implantable bodily fluid drainage valve.

6. The method according to claim 4, wherein the lock stops and the corresponding setting pockets are equal in number.

7. The method according to claim 1, wherein the determining step is performed following programming of the desired valve setting of the implantable bodily fluid drainage valve.

8. The method according to claim 1, wherein the determined step of performed prior to a magnetic resonance imaging procedure.

9. The method according to claim 1, wherein the generating the alert step comprises the step of generating a visual and/or tactile indicator.

10. The method according to claim 4, wherein the magnetic field resistance mechanism is engaged when the plurality of downward projecting teeth are properly seated in the corresponding setting pockets; whereas the magnetic field resistance mechanism is not properly engaged when any of the plurality of downward projecting teeth are resting on one of the lock stops.

11. The method according to claim 2, wherein the rotating construct is rotatably mounted in a housing about an axis; a substantially cylindrical central part is fixedly mounted on the axis; wherein the rotating construct includes lateral branches on either side of the axis for moving parts each housing a respective one of the pair of primary magnetic elements with opposing faces of opposite polarity; a mating lead in element extending respectively from each of the moving parts; the moving parts are displacable linearly inside the rotating construct in a substantially radial direction thereof to actuate the mating lead in element in a circular succession of pockets defined radially inward along an outer perimeter of the substantially cylindrical central part.

12. The method according to claim 11, wherein the mechanical resistance mechanism is engaged when the mating lead in element is seated in one of the pockets; whereas the magnetic field resistance mechanism is not engaged when the mating lead in element is resting along the outer perimeter of the substantially cylindrical central part between the pockets adjacent to one another.

13. The method according to claim 11, wherein the determining step comprises:
  detecting an angular position of one of the pair of primary magnetic elements
  comparing the detected angular position to the predetermined angular spacing of the respective notches; wherein if the detected angular position matches the predetermined angular spacing of one of the respective pockets the magnetic field resistance mechanism is deemed to be properly engaged; otherwise, if the detected angular position does not match the predetermined angular spacing of any of the respective pockets the magnetic field resistance mechanism is deemed not to be properly engaged.

14. The method according to claim 11, wherein the determining step comprises:
  detecting a center of each of the pair primary magnetic elements;
  calculating a distance separation between the detected center of each of the pair of primary magnetic elements;
  comparing the calculated distance separation to a predetermined locking value; wherein if the calculated distance separation is equal to the predetermined locking value then the magnetic field resistance mechanism is deemed properly engaged; otherwise if the calculated distance separation is greater than the predetermined locking value then the magnetic field resistance mechanism is deemed not to be properly engaged.

\* \* \* \* \*

UNITED STATES PATENT AND TRADEMARK OFFICE
CERTIFICATE OF CORRECTION

PATENT NO. : 10,850,081 B2
APPLICATION NO. : 15/708549
DATED : December 1, 2020
INVENTOR(S) : Boden, Jr. et al.

Page 1 of 1

It is certified that error appears in the above-identified patent and that said Letters Patent is hereby corrected as shown below:

In the Claims

Column 18, Claim 4, Line 6, change "the" to --a--.

Column 19, Claim 8, Line 2, change "of" to --is--.

Column 20, Claim 12, Line 2, change "mechanical" to --magnetic field--.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*